US012721842B2

(12) United States Patent
Kwon et al.

(10) Patent No.: US 12,721,842 B2
(45) Date of Patent: Sep. 1, 2026

(54) CINNAMAMIDE DERIVATIVES AND USE THEREOF

(71) Applicant: KOREA RESEARCH INSTITUTE OF BIOSCIENCE AND BIOTECHNOLOGY, Daejeon (KR)

(72) Inventors: Byoung-Mog Kwon, Daejeon (KR); Dong Cho Han, Daejeon (KR); Yujin Lee, Daejeon (KR); Jiyeon Choi, Daejeon (KR); Kyung Chan Park, Daejeon (KR); Seong-Hwan Park, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 365 days.

(21) Appl. No.: 18/561,624

(22) PCT Filed: Jun. 7, 2023

(86) PCT No.: PCT/KR2023/007746
§ 371 (c)(1),
(2) Date: Nov. 16, 2023

(87) PCT Pub. No.: WO2023/249288
PCT Pub. Date: Dec. 28, 2023

(65) Prior Publication Data

US 2025/0082620 A1 Mar. 13, 2025

(30) Foreign Application Priority Data

Jun. 22, 2022 (KR) ........................ 10-2022-0076360

(51) Int. Cl.

| | |
|---|---|
| ***A61K 31/4409*** | (2006.01) |
| ***A61K 31/165*** | (2006.01) |
| ***A61K 45/06*** | (2006.01) |
| ***A61P 35/00*** | (2006.01) |
| ***C07C 235/80*** | (2006.01) |
| ***C07D 213/30*** | (2006.01) |

(52) U.S. Cl.
CPC ........ *A61K 31/4409* (2013.01); *A61K 31/165* (2013.01); *A61K 45/06* (2013.01); *A61P 35/00* (2018.01); *C07C 235/80* (2013.01); *C07D 213/30* (2013.01)

(58) Field of Classification Search
CPC .. A61K 31/4409; A61K 31/165; A61K 45/06; C07C 235/80; A61P 35/00; C07D 213/30
USPC .......................................................... 514/277
See application file for complete search history.

(56) References Cited

U.S. PATENT DOCUMENTS

2014/0329901 A1 11/2014 Priebe et al.

FOREIGN PATENT DOCUMENTS

| | | | |
|---|---|---|---|
| CN | 103880707 | A | 6/2014 |
| KR | 10-2015-0144679 | A | 12/2015 |
| WO | 2020/205470 | A1 | 10/2020 |

OTHER PUBLICATIONS

Cancer [online], [retrieved on Jul. 6, 2007] Retrieved from the Internet, URL: http://www.nim.nih.gov/medlineplus/cancer.html (Year: 2007).*

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

Young Hwam Kim et al., "Piperlongumine derivative, CG-06, inhibits STAT3 activity by direct binding to STAT3 and regulating the reactive oxygen species in DU145 prostate carcinoma cells", Bioorganic & Medicinal Chemistry, Letters, 2018, vol. 28, pp. 2566-2572.

Alex D. Waldman et al., "A guide to cancer immunotherapy: from T cell basic Science to clinical practice", Nature Reviews, Nov. 2020, vol. 20, pp. 651-668.

Defne Bayik et al., "Cancer stem cell-immune cell crosstalk in tumour progression", Nature Reviews, 11 pages.

Golnaz Morad et al., "Hallmarks of response, resistance, and toxicity to immune checkpoint blockade", Cell 184, Oct. 14, 2021, pp. 5309-5337.

Hyuna Sung, Ph.D et al., "GLOBOCAN Estimates of Incidence and Mortality Worldwide for 36 Cancers in 185 Countries", Global Cancer Statistics 2020, May/Jun. 2021, vol. 71 No. 3, pp. 209-249.

Katherine Bourzac, "Three known unknowns even as cancer therapies improve, basic questions about drug resistance, tumour spread and the role of normal tissue remain unanswered", Nature, May 29, 2014, vol. 509, pp. S69-S71.

Mohamed El-Tanani et al., "Importance of STAT3 Signalling in cancer, metastasis and therapeutic interventions", Cellular Signaling, 2022, vol. 92, pp. 1-7.

Melissa R. Junttila et al., "Influence of tumour micro-environment heterogeneity on therapeutic response", Nature, Sep. 19, 2013, vol. 501, pp. 346-354.

Philip Cohen et al., "Kinase drug discovery 20 years after imatinib: progress and future directions", Nature Reviews, Jul. 2021, vol. 20, pp. 551-569.

Po-Chang Shih et al., "Role of STAT3 signaling transduction pathways in cancer stem cell-associated chemoresistance", Drug Discovery Today, Jun. 2021, vol. 26 No. 6, pp. 1450-1458.

Yuanyuan Zhang et al., "The history and advances in cancer immunotherapy: understanding the characteristics of tumor-infiltrating immune cells and their therapeutic implications", Cellular & Molecular Immunology, Jul. 1, 2020, vol. 17, pp. 807-821.

* cited by examiner

*Primary Examiner* — Kristin A Vajda
(74) *Attorney, Agent, or Firm* — Sughrue Mion, PLLC

(57) ABSTRACT

The present disclosure relates to novel cinnamamide derivatives and use thereof in preventing or treating cancer.

12 Claims, 15 Drawing Sheets

[FIG. 1]
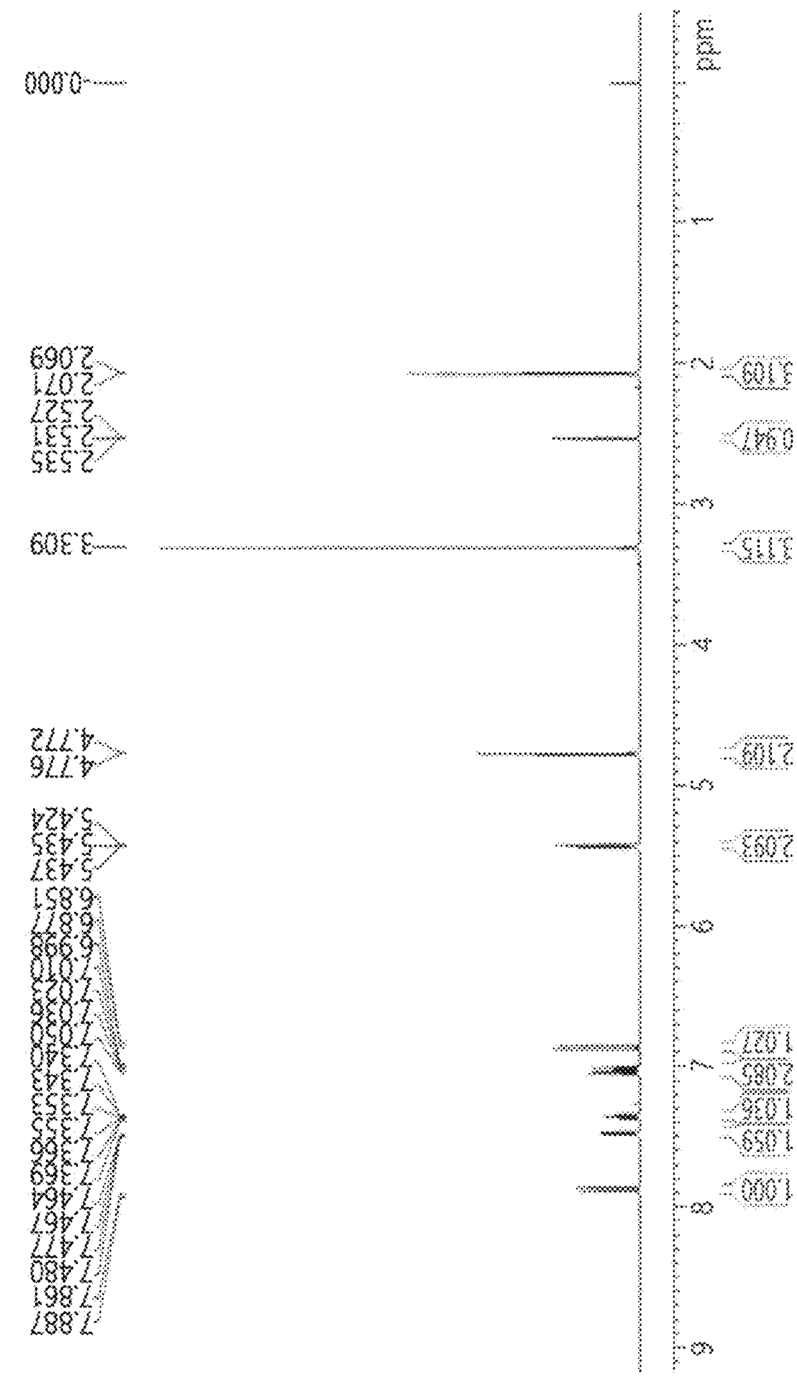

[FIG. 2]
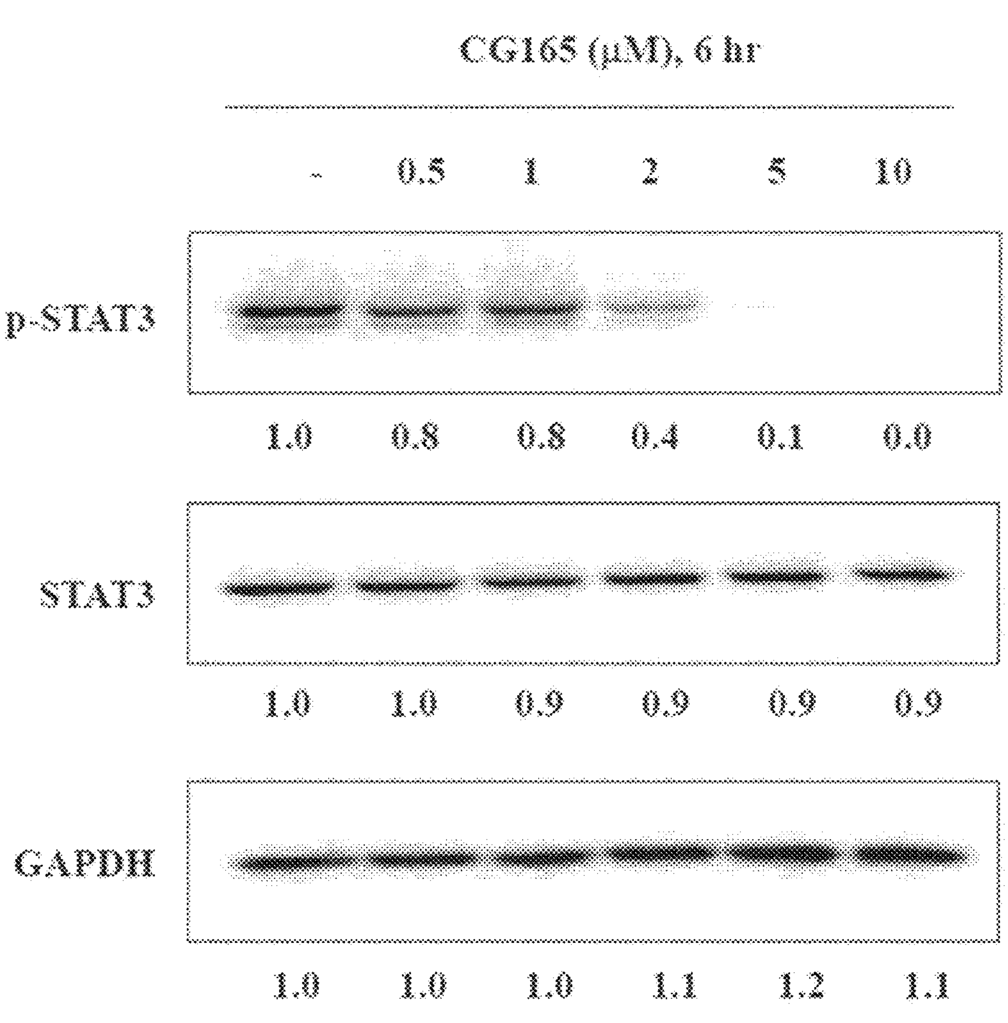

[FIG. 3]
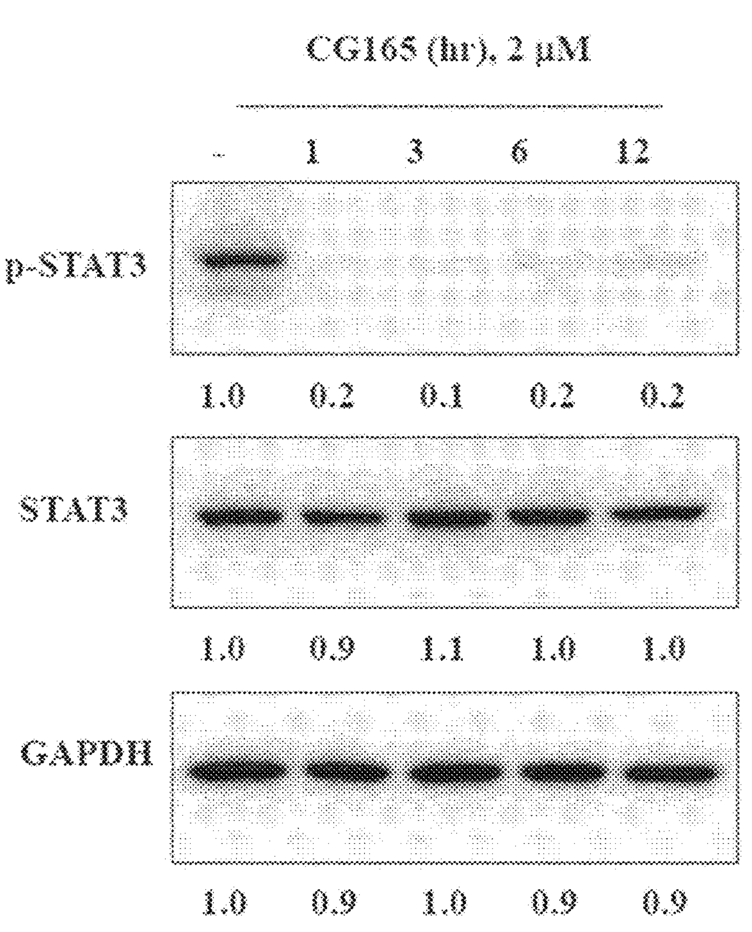

[FIG. 4]
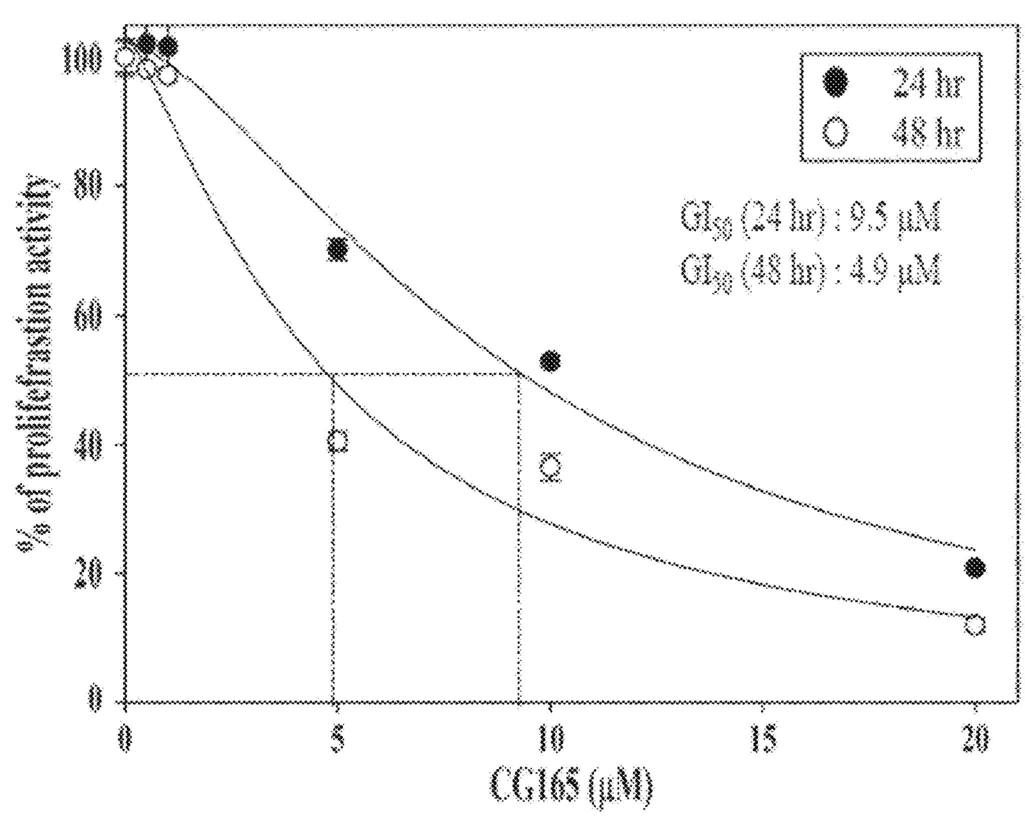

[FIG. 5]
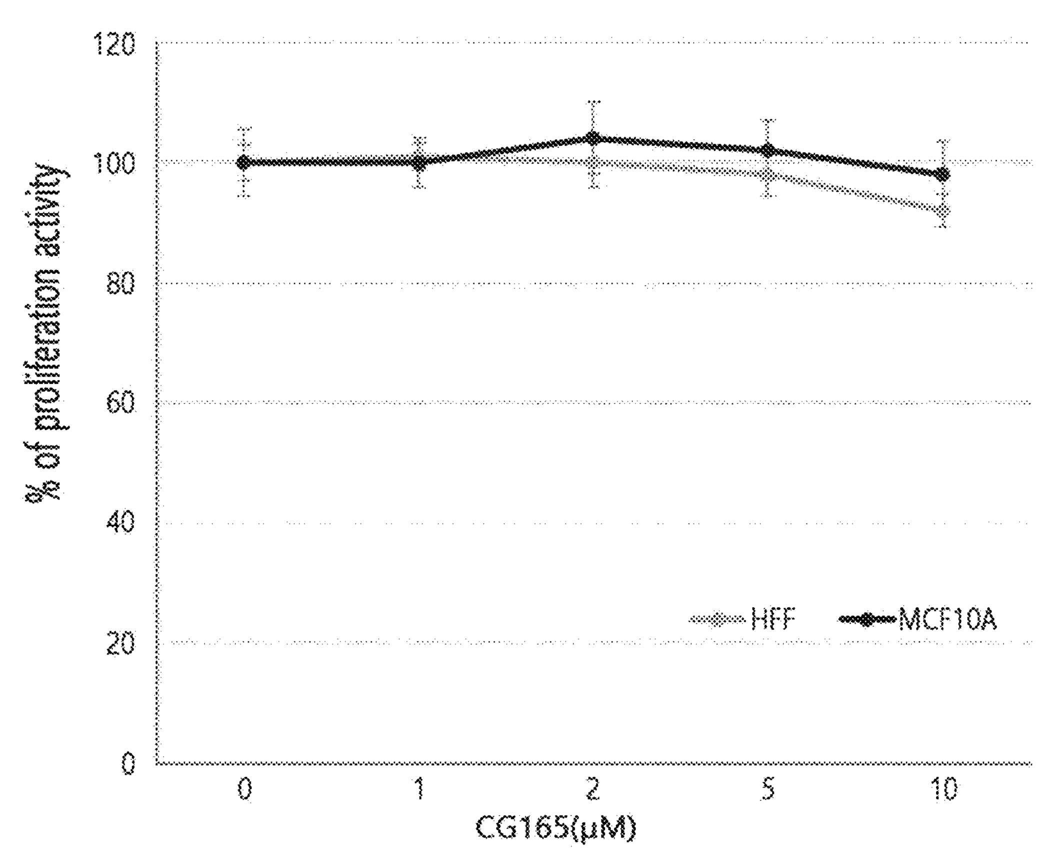

[FIG. 6]
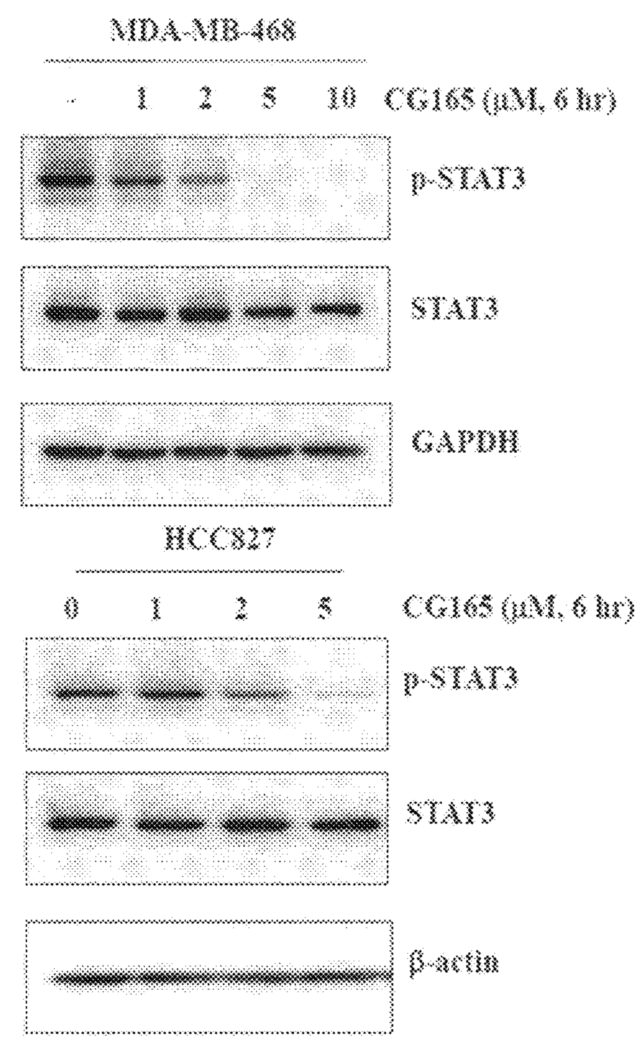

[FIG. 7]
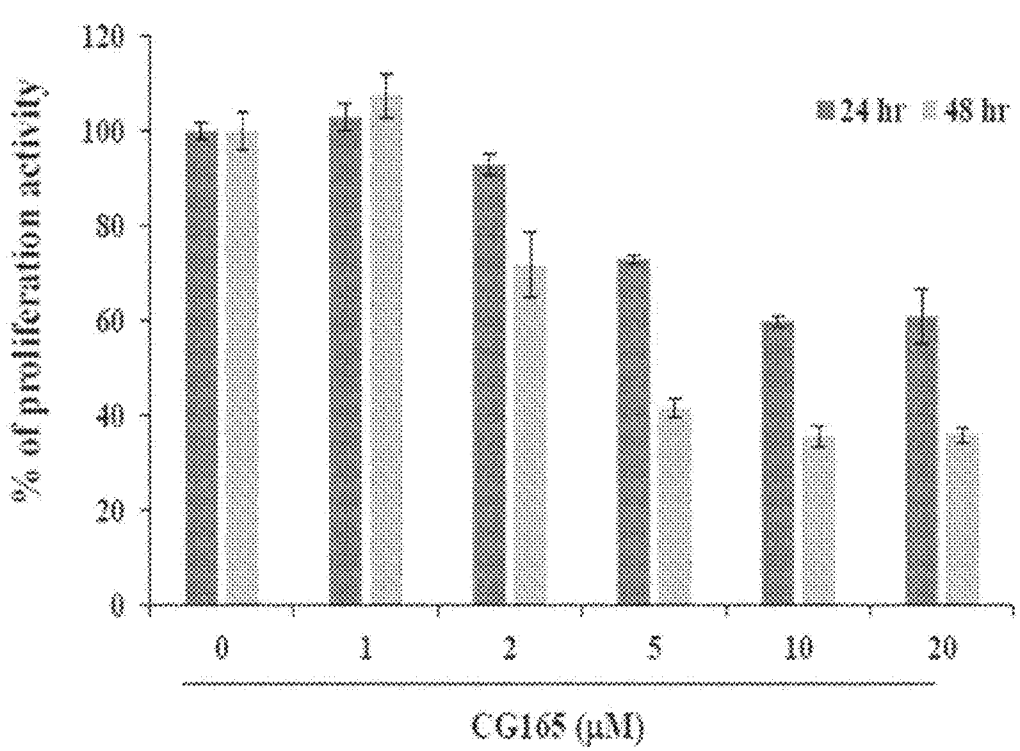

[FIG. 8]
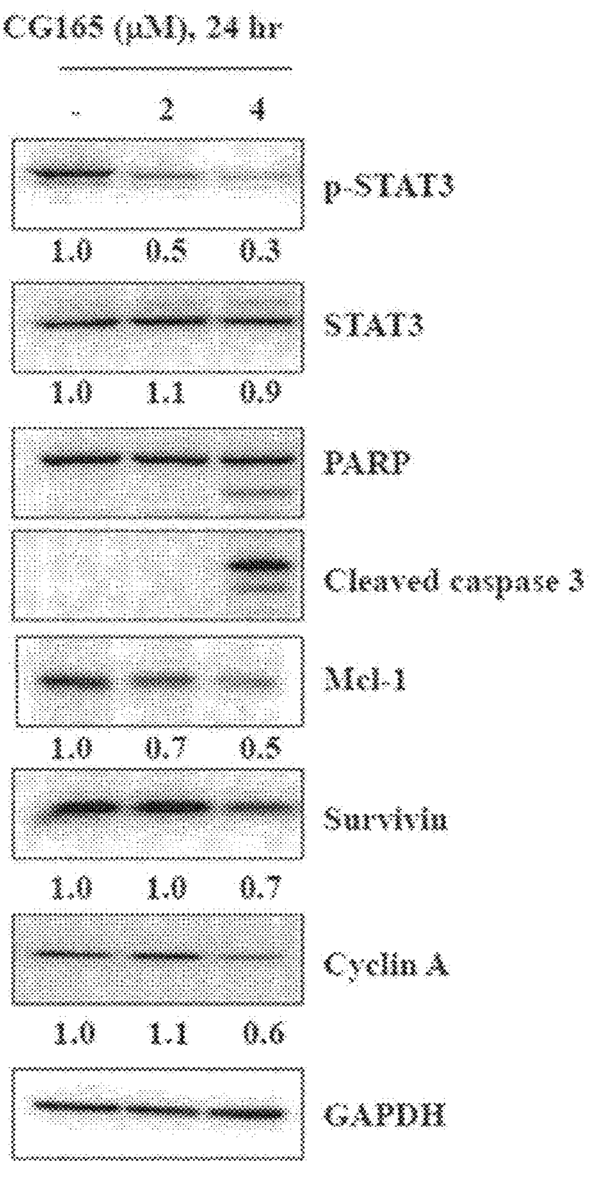

[FIG. 9]
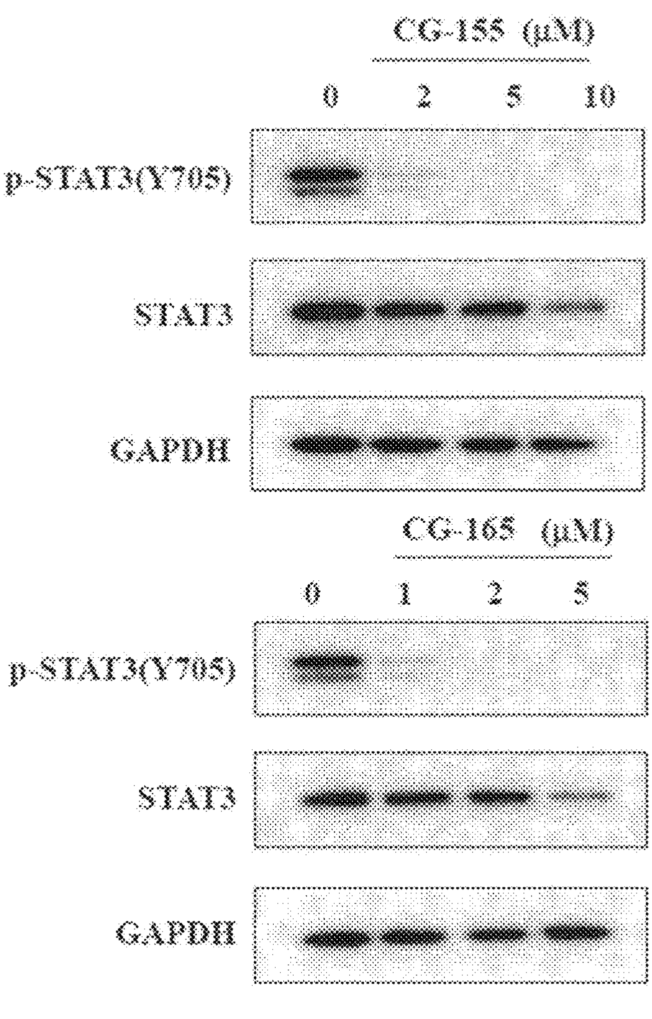

[FIG. 10]
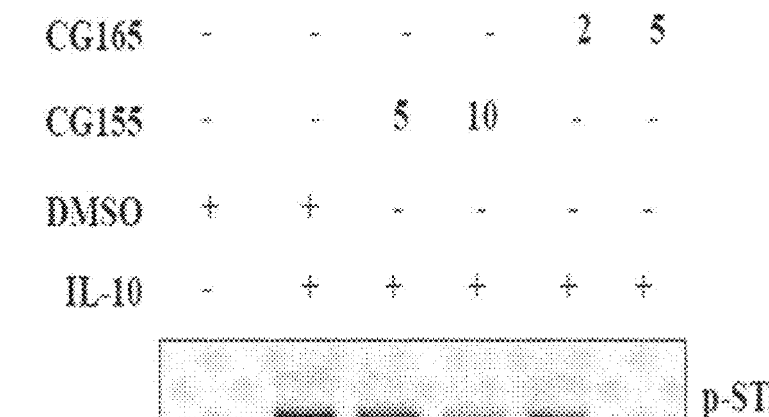
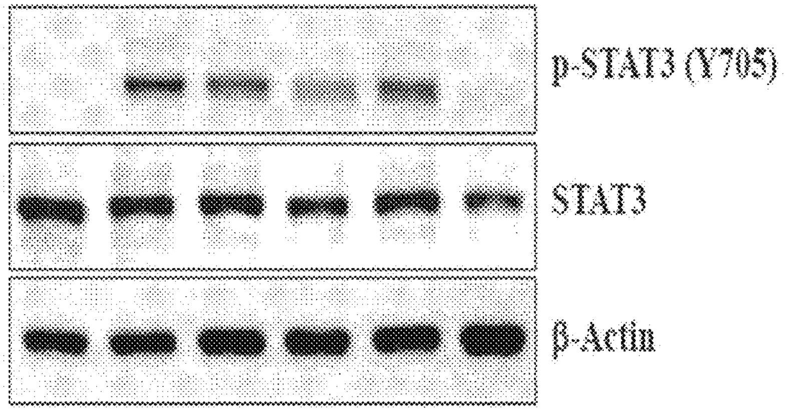

[FIG. 11]
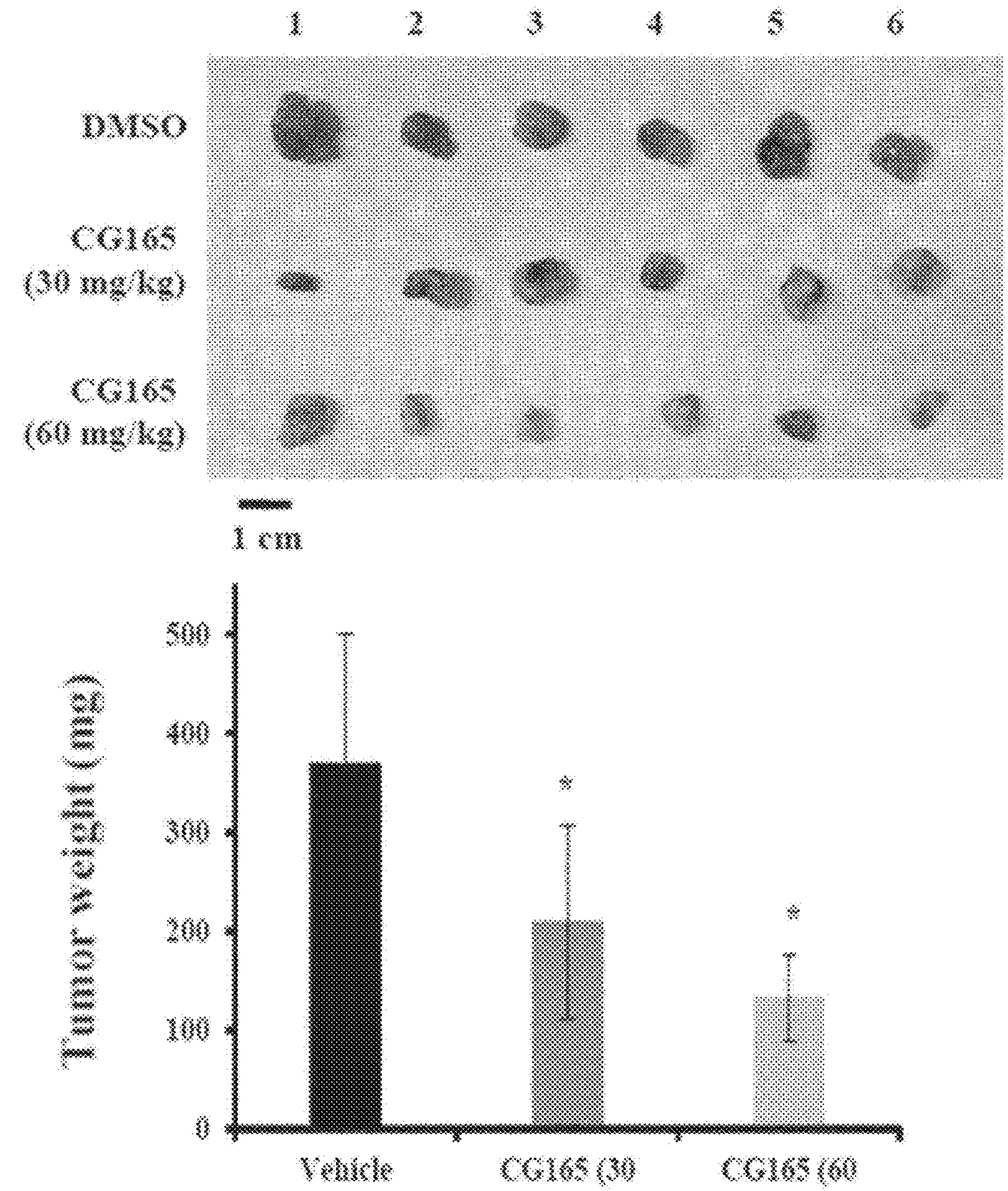

[FIG. 12]
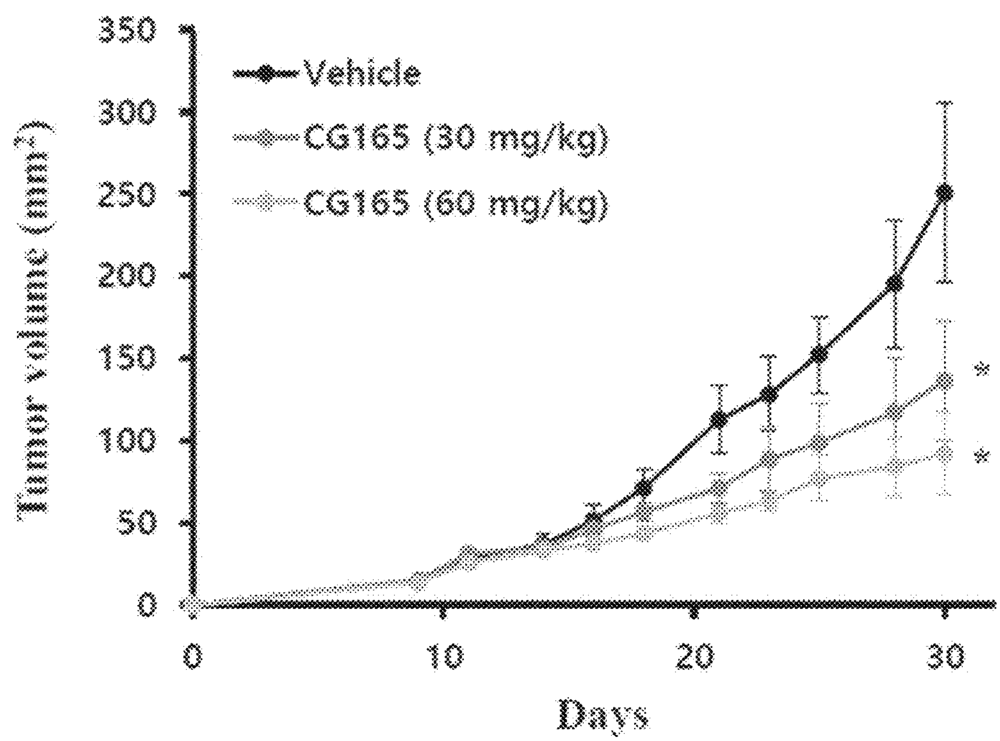

[FIG. 13]
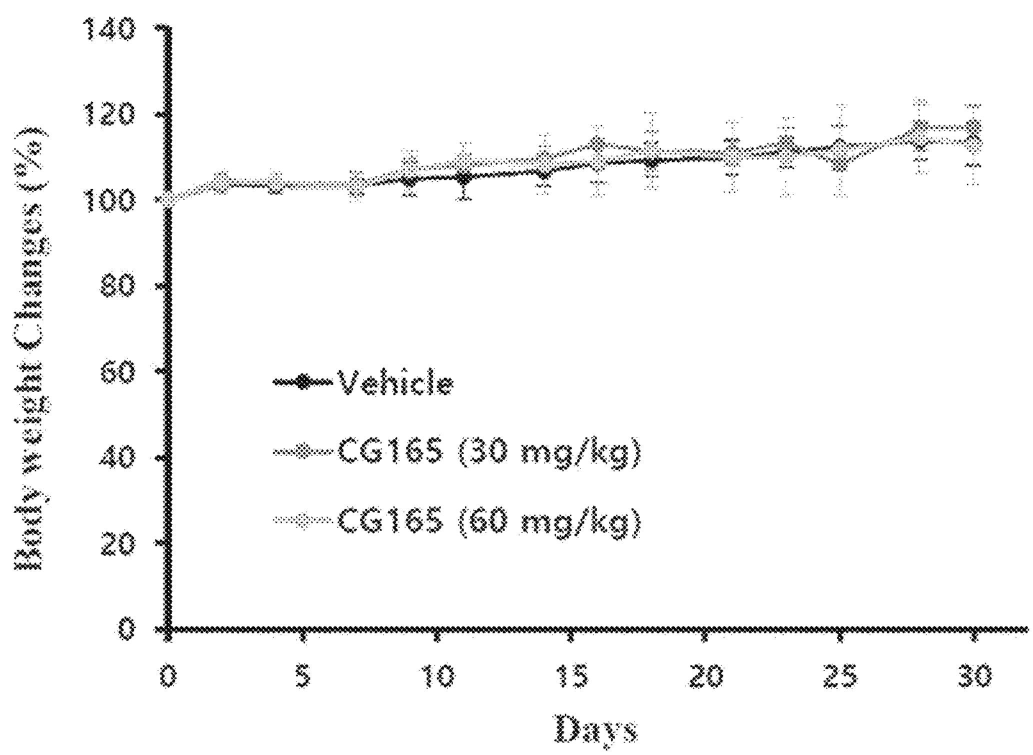

[FIG. 14]
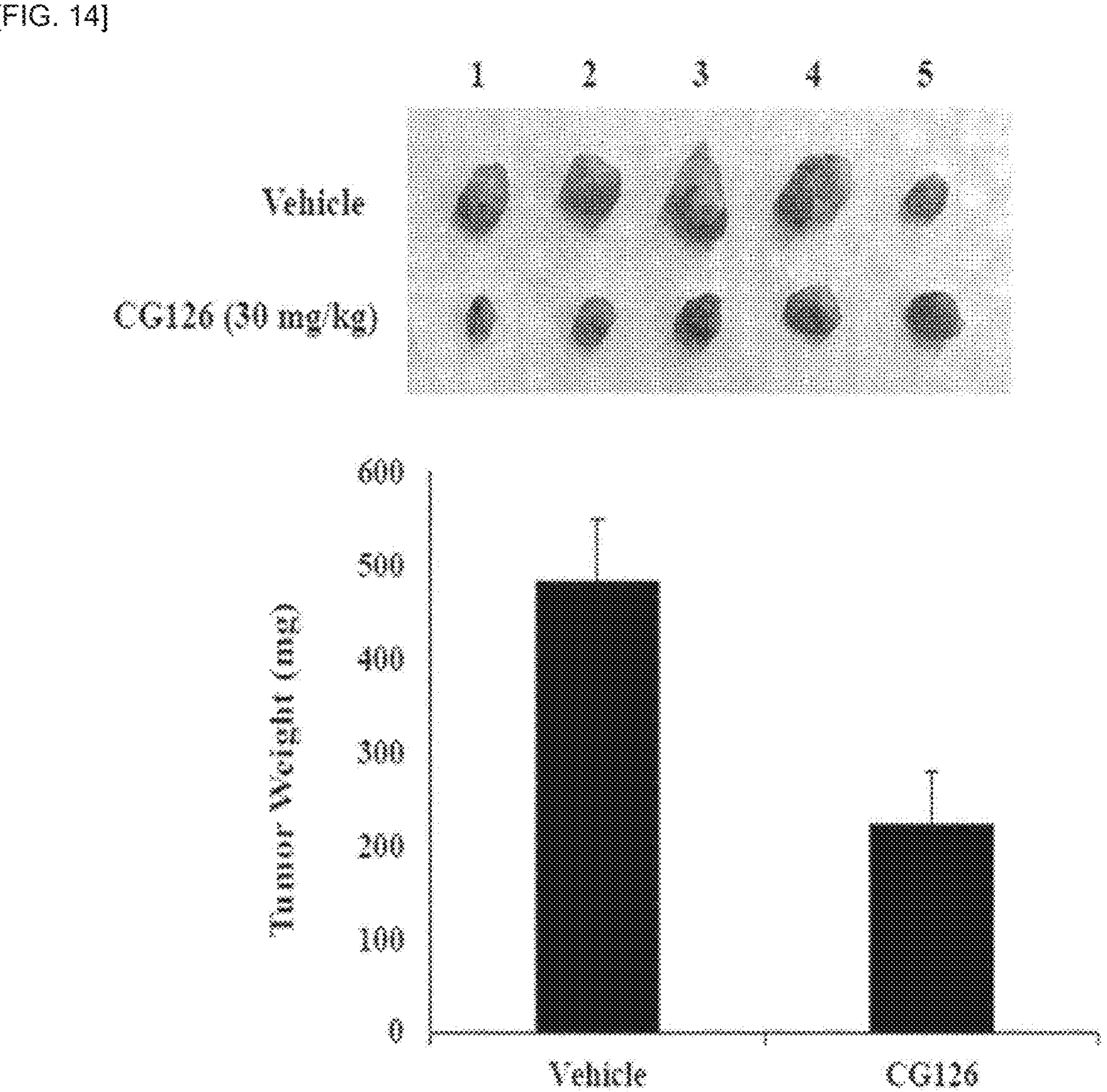

[FIG. 15]

(Mean ± SD : g)

| Group | Doses (mg/kg) | Days after treatment | | | | |
|---|---|---|---|---|---|---|
| | | 0 | 1 | 2 | 4 | 7 |
| Vehicle | 0 | 27.5 ± 0.9 | 27.9 ± 0.6 | 29.3 ± 1.0 | 30.4 ± 1.4 | 31.4 ± 1.5 |
| CG165 | 100 | 27.5 ± 0.6 | 27.8 ± 0.7 | 29.3 ± 0.8 | 30.2 ± 1.1 | 31.3 ± 1.0 |
| | 200 | 27.5 ± 0.9 | 27.8 ± 1.2 | 29.2 ± 1.3 | 30.1 ± 1.3 | 31.3 ± 1.1 |
| | 300 | 27.6 ± 0.5 | 27.9 ± 0.2 | 29.2 ± 0.8 | 30.2 ± 1.1 | 31.3 ± 0.9 |

CINNAMAMIDE DERIVATIVES AND USE THEREOF

This Application is a National Stage of International Application No. PCT/KR2023/007746 filed Jun. 7, 2023, claiming priority based on Korean Patent Application No. 10-2022-0076360 filed Jun. 22, 2022, the entire disclosures of which are incorporated herein by reference.

TECHNICAL FIELD

The present disclosure relates to novel cinnamamide derivatives and use thereof in preventing or treating cancer.

BACKGROUND ART

According to statistics released in May 2021 (Global Cancer Statistics 2020), 19.3 million new cancer patients are diagnosed worldwide as of 2020, and the number of deaths due to cancer reaches 10 million (H. Sung et al., *CA Cancer J. Clin.* 71, 209, 2021).

Since the 1940s, when the first chemical anticancer drugs were used, various anticancer drugs have been developed with the goal of fundamentally eliminating cancer cells and ultimately conquering cancer. The first-generation anticancer drugs developed until the mid-1990s inhibited the growth of rapidly growing cancer cells, but side effects that also affected normal cells became a problem. To solve this problem, the second-generation anticancer drugs, i.e., targeted anticancer drugs, which selectively attack cancer cells, have been developed since the late 1990s, but a problem was discovered wherein resistance developed after a certain period of time, which decreased drug effectiveness (P. Cohen et al. *Nature Rev. Drug Discov.* 20, 551, 2021).

To solve such problem, the third-generation anticancer drugs, i.e., immune anticancer drugs, have been developed since the 2010s. Immunotherapy is a treatment method that suppresses or eliminates the growth of cancer through activation and suppression of the immune system in the body, and the method includes immune checkpoint inhibitors, immune cell therapy, therapeutic antibodies, etc. Immune checkpoint inhibitors are drugs that attack cancer cells through activation of T cells by blocking the activation of immune checkpoint proteins involved in T cell suppression, and examples thereof include CTLA-4, PD-1, PD-L1 inhibitors, etc. Immune cell therapy is a drug that strengthens cellular immunity against cancer cells by collecting, strengthening and modifying, and then injecting T cells in the body through autologous cell transplantation (ACT), and examples thereof include CAR T cell therapy and natural killer cell (NK cell) therapy, which induces the death of cancer cells by inducing innate immune response, etc. Additionally, therapeutic antibodies are drugs that attack cancer cells by releasing the drug when an antibody-drug complex binds to cancer cells, and examples thereof may include antibody-drug conjugates (ADCs), etc. (Y. Zhang, et al., *Cell. Mol. Immunol.* 17, 807, 2020).

Cancer immunotherapy is a new anticancer drug that connects chemotherapy and targeted therapy, and has achieved clinical success by dramatically increasing the survival rate of patients (A. D. Waldman, et al., *Nature Rev. Immunol.* 20, 651, 2020). However, the low immune reactivity of cancer cells is believed to be the cause of decreasing response rate to cancer immunotherapy, especially immune checkpoint inhibitors. In particular, the overall reactivity in solid cancer is low (e.g., 15% to 20% in lung cancer), and side effects and resistance to cancer immunotherapy have been reported, and thus, the limitation thereof have been clearly seen (G. Morad, et al., *Cell* 184, 5309, 2021).

An article titled "Three known unknowns" published in *Nature* in 2014 stated that although there have been advances in cancer treatment, there are three things that remain unknown about cancer: anticancer drug resistance, cancer metastasis, and the role of normal cells around cancer cells, i.e., tumor microenvironment (K. Bourzac, *Nature* 509, S69, 2014). It is believed that humanity will be free from the disease called cancer only when the answers to the above three things and the development of regulators are achieved.

The development of anticancer drug resistance is broadly classified into two types: intrinsic resistance, in which cancer cells do not respond to drugs due to the presence of drug-resistant factors in cancer cells from the beginning, and acquired resistance, in which the drug exhibits anticancer effects for a while, but no longer responds to cancer cells due to mutations that occur during continuous administration of the drug or interaction with other signaling systems.

There are many causes of resistance, and among them, the tumor microenvironment has recently become the subject of interest. Tumors themselves have very complex heterogeneity and interact with a wide variety of cells around them, and this is collectively referred to as the tumor microenvironment (TME). The tumor microenvironment includes not only tumor cells but also normal epithelial cells, endothelial cells, fibroblasts, and immune cells. These cells are organically connected to each other and are closely related to anticancer drug resistance (M. R. Junttila, *Nature* 501, 346, 2013). For example, important immune cells in the tumor microenvironment include regulatory T cells (Treg), myeloid-derived suppressor cells (MDSC), cancer-associated fibroblasts (CAF), natural killer cells (NK cells), etc.

Meanwhile, signal transducer and activator of transcription 3 (STAT3) has been identified as an important protein in intracellular signal transduction whose function is regulated by cytokines or hormones and which is involved in cell growth and differentiation, etc. It has been verified through many studies that the continuous activity of STAT3 can promote the survival and metastasis of tumor cells (M. El-Tanani, et al., *Cellular Signalling* 92, 100275, 2022). In addition, it has been reported in various studies over the past 10 years that STAT3 is related to the induction of anticancer drug resistance and the maintenance of cancer stem cells (P. Shih, et al., *Drug Discov. Today,* 26, 1450, 2021). As mentioned earlier, STAT3 is involved in regulating the functions of regulatory T cells, myeloid-derived suppressor cells, and natural killer cells in the tumor microenvironment, especially immune cells, which are the main causes of anticancer drug resistance (D. Bayik, et al., *Nature Rev. Cancer,* 21, 526, 2021).

In this regard, research for developing drugs that overcome the resistance of anticancer drugs and increase drug activity by activating anticancer immunity, which converts the tumor microenvironment from a cold cancer that does not respond to cancer immunotherapy to a hot cancer that responds to cancer immunotherapy, is necessary.

Under such circumstances, the present inventors have made diligent efforts to develop a method that can more effectively treat or prevent cancer by controlling the growth of cancer cells and the cancer cell microenvironment. As a result, they synthesized novel cinnamamide derivatives and confirmed that the compounds inhibited STAT3 activity, thereby exhibiting the effects of inhibiting the growth of cancer cells and increasing the activity of immune cells that play an important role in the tumor microenvironment, and completed the present disclosure.

DISCLOSURE

Technical Problem

The present inventors developed a novel cinnamamide derivative that can be effectively used in the prevention or treatment of cancer, thereby completing the present disclosure.

Technical Solution

It is one object of the present disclosure to provide a compound represented by Chemical Formula 1 below, or a pharmaceutically acceptable salt thereof:

[Chemical Formula 1]

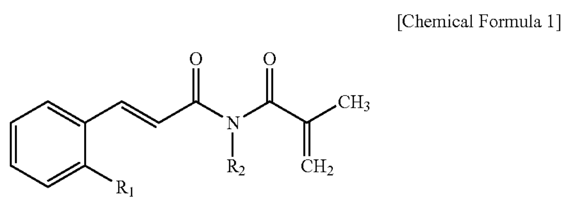

In Chemical Formula 1, $R_1$ is $C_{1-6}$ alkyl; hydroxy; halogen; $C_{1-6}$ alkynyloxy; or unsubstituted or substituted $C_{1-6}$ alkoxy; wherein the substituted $C_{1-6}$ alkoxy contains $C_{1-6}$ aryl or 5- to 14-membered heteroaryl as a substituent, wherein the heteroaryl contains one or more O, N, or S, and $R_2$ is hydrogen or alkyl.

It is another object of the present disclosure to provide a pharmaceutical composition for preventing or treating cancer, including a compound represented by Chemical Formula 1 above, or a pharmaceutically acceptable salt thereof, as an active ingredient.

It is still another object of the present disclosure to provide a method for preventing or treating cancer: including administering a pharmaceutical composition containing a compound represented by Chemical Formula 1 below, or a pharmaceutically acceptable salt thereof, as an active ingredient, into a subject excluding a human.

It is yet another object of the present disclosure to provide a food composition for preventing or improving cancer, including a compound represented by Chemical Formula 1 above, or a sitologically acceptable salt thereof, as an active ingredient.

It is even another object of the present disclosure to provide a feed composition for preventing or improving cancer, including a compound represented by Chemical Formula 1 above, or a sitologically acceptable salt thereof, as an active ingredient.

Advantageous Effects

The novel compounds of the present disclosure or pharmaceutically acceptable salts exhibits the effects of inhibiting the growth of cancer cells and increasing the activity of immune cells in the tumor microenvironment by inhibiting STAT3 activity, and thus can be effectively used in the prevention or treatment of cancer.

BRIEF DESCRIPTION OF THE DRAWING

FIG. 1 shows $^1$H-NMR data of compound CG165 according to an embodiment of the present disclosure.

FIG. 2 is a diagram showing that STAT3 phosphorylation is inhibited in prostate cancer cell line by the compound CG165 of the present disclosure in a concentration-dependent manner.

FIG. 3 is a diagram showing that STAT3 phosphorylation is inhibited in prostate cancer cell line by the compound CG165 of the present disclosure in a time-dependent manner.

FIG. 4 shows the results of measuring the cell growth inhibitory activity of the compound CG165 of the present disclosure in prostate cancer cell line.

FIG. 5 is a diagram showing the results of verifying that the compound CG165 of the present disclosure has no cell growth inhibitory activity in normal cell line.

FIG. 6 is a diagram showing that STAT3 phosphorylation is inhibited in breast and lung cancer cell lines by the compound CG165 of the present disclosure in a concentration-dependent manner.

FIG. 7 shows the results of measuring the cell growth inhibitory activity of the compound CG165 of the present disclosure in breast cancer cell line.

FIG. 8 is a diagram showing that the expression of STAT3 target proteins is suppressed and cell death is induced in cancer cell lines by the compound CG165 of the present disclosure.

FIG. 9 is a diagram showing that STAT3 phosphorylation is inhibited in natural killer cells (NKL), which are immune cells, by the compound CG155 or CG165 of the present disclosure.

FIG. 10 is a diagram showing that STAT3 phosphorylation is inhibited in bone marrow-derived macrophages (BMDM), which are immune cells, by the compound CG155 or CG165 of the present disclosure.

FIG. 11 is a diagram showing the results of measuring the change in weight of cancer tissue when the compound CG165 of the present disclosure was orally administered to mice subcutaneously implanted with prostate cancer.

FIG. 12 is a diagram showing the results of measuring the change in size of cancer tissue when the compound CG165 of the present disclosure was orally administered to mice subcutaneously implanted with prostate cancer.

FIG. 13 is a diagram showing the results of measuring the change in body weight of animals when the compound CG165 of the present disclosure was orally administered to mice subcutaneously implanted with prostate cancer.

FIG. 14 is a diagram showing the results of measuring the change in weight of cancer tissue when the compound CG126 of the present disclosure was intraperitoneally administered to mice subcutaneously implanted with prostate cancer.

FIG. 15 is a diagram showing the results of a single oral dose toxicity verification test for the compound CG165 of the present disclosure.

DETAILED DESCRIPTION OF PREFERRED EMBODIMENTS

Hereinafter, the present disclosure will be described in detail. Meanwhile, each description and embodiment disclosed herein can be applied to other descriptions and embodiments, respectively. That is, all combinations of various elements disclosed herein fall within the scope of the present disclosure. Further, the scope of the present disclosure is not limited by the specific description described below.

One aspect of the present disclosure provides a compound represented by Chemical Formula 1 below, or a pharmaceutically acceptable salt thereof:

[Chemical Formula 1]

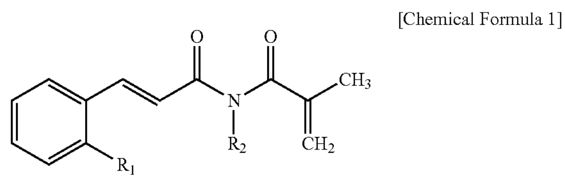

In Chemical Formula 1, $R_1$ is $C_{1-6}$ alkyl; hydroxy; halogen; $C_{1-6}$ alkynyloxy; or unsubstituted or substituted $C_{1-6}$ alkoxy; wherein the substituted $C_{1-6}$ alkoxy contains $C_{1-6}$ aryl or 5- to 14-membered heteroaryl as a substituent, wherein the heteroaryl contains one or more O, N, or S, and $R_2$ is hydrogen or alkyl.

For example, in the compound of the present disclosure, $R_1$ may be $—OCH_3$, $—CH_3$, —OH, —Cl,

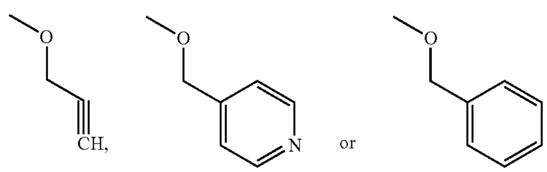

or and $R_2$ may be hydrogen or methyl, but is not limited thereto.

For example, the compound of the present disclosure may be a compound having the following compound structures.

TABLE 1

| Name of Compounds | Compound Structure |
| --- | --- |
| CG126 | 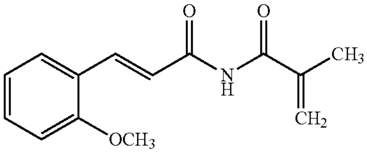 [SMILES: C=C(C)C(=O)NC(=O)/C=C/c1ccccc1OC] |
| CG127 | 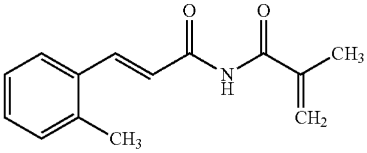 [SMILES: C=C(C)C(=O)NC(=O)/C=C/c1ccccc1C] |
| CG133 | 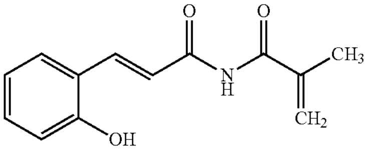 [SMILES: C=C(C)C(=O)NC(=O)/C=C/c1ccccc1O] |

TABLE 1-continued

| Name of Compounds | Compound Structure |
| --- | --- |
| CG155 | 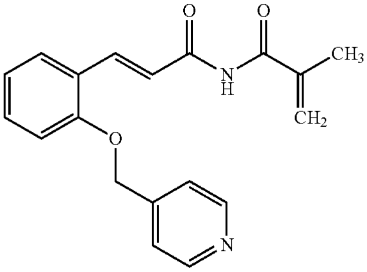 [SMILES: C=C(C)C(=O)NC(=O)/C=C/c1ccccc1OCc1ccncc1] |
| CG164 | 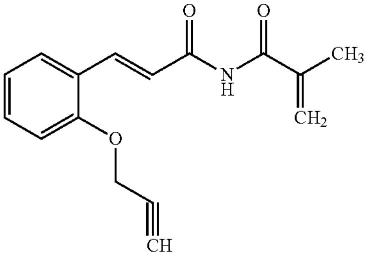 [SMILES: C#CCOc1ccccc1/C=C/C(=O)NC(=O)C(=C)C] |
| CG165 | 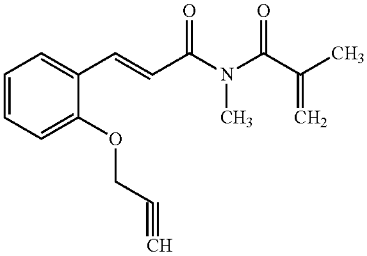 [SMILES: C#CCOc1ccccc1/C=C/C(=O)N(C)C(=O)C(=C)C] |
| CG168 | 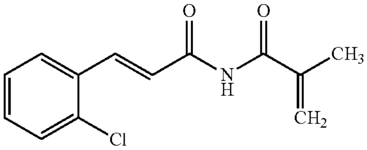 [SMILES: C=C(C)C(=O)NC(=O)/C=C/c1ccccc1Cl] |
| CG187 | 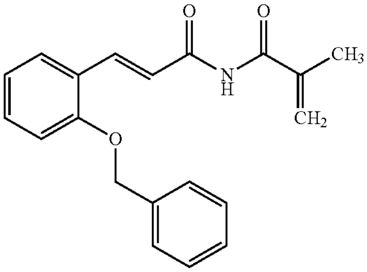 [SMILES: C=C(C)C(=O)NC(=O)/C=C/c1ccccc1OCc1ccccc1] |

Meanwhile, the compound of the present disclosure may exist in the form of a pharmaceutically acceptable salt. An acid addition salt formed by pharmaceutically acceptable free acid may be useful as the salt. As used herein, the term "pharmaceutically acceptable salt" refers to any organic or inorganic addition salt of the compound, which has a concentration such that it exhibits an effective action that is relatively non-toxic and harmless to patients, whose side effects caused by the salt do not impair the beneficial effect of the compound represented by Chemical Formula 1.

The acid addition salt may be prepared by a conventional method, for example, by dissolving the compound in an excessive amount of acid aqueous solution, and then precipitating the salt using a water-miscible organic solvent such as methanol, ethanol, acetone or acetonitrile. An acid or alcohol (e.g., glycol monomethyl ether) in the equal molar amount of the compound and water may be heated, and then the mixture may be dried by evaporation, or the precipitated salt may be suction-filtered.

Herein, as the free acid, an organic acid and an inorganic acid may be used. As the inorganic acid, hydrochloric acid, phosphoric acid, sulfuric acid, nitric acid, tartaric acid, etc. may be used, and as the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc., may be used, but are not limited thereto.

Further, a pharmaceutically acceptable metal salt may be prepared using a base. An alkali metal salt or an alkaline earth metal salt is, for example, obtained by dissolving a compound in an excessive amount of an alkali metal hydroxide or an alkaline earth metal hydroxide solution, filtering undissolved compound salts, and then evaporating and drying the filtrate. Herein, it is preferable that a sodium, potassium or calcium salt is prepared as the metal salt in a pharmaceutical aspect, but is not limited thereto. In addition, a silver salt corresponding to the metal salt may be obtained by allowing an alkali metal salt or an alkaline earth metal salt to react with a suitable silver salt (e.g., silver nitrate).

The pharmaceutically acceptable salt of the compound of the present disclosure may include a salt of an acidic or a basic group, which can be present in the compound of Chemical Formula 1, unless otherwise specifically indicated. For example, the pharmaceutically acceptable salt may include a sodium salt, a calcium salt, and a potassium salt of a hydroxy group, and other pharmaceutically acceptable salt of amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc. Further, these salts may be prepared by a preparation method known in the related art.

The salt of the cinnamamide derivative compound of the present disclosure is a pharmaceutically acceptable salt, and any salt of the cinnamamide derivatives that exhibits pharmacological activity equivalent to that of the cinnamamide derivative compound can be used without limitation.

In addition, the compound represented by Chemical Formula 1 according to the present disclosure include not only pharmaceutically acceptable salts thereof, but also all solvates or hydrates and all possible stereoisomers that can be prepared therefrom. The solvates and stereoisomers of the compound represented by Chemical Formula 1 can be prepared from the compound represented by Chemical Formula 1 using a conventional method known in the art.

In addition, the compound represented by Chemical Formula 1 according to the present disclosure may be prepared either in a crystalline form or in a non-crystalline form, and when the compound of Chemical Formula 1 is prepared in a crystalline form, it may be optionally hydrated or solvated. In the present disclosure, the compound of Chemical Formula 1 may not only include a stoichiometric hydrate, but also include a compound containing various amounts of water. The solvate of the compound of Chemical Formula 1 according to the present disclosure includes both stoichiometric solvates and non-stoichiometric solvates.

Another aspect of the present disclosure provides a pharmaceutical composition for preventing or treating cancer, including a compound represented by Chemical Formula 1 above, or a pharmaceutically acceptable salt thereof, as an active ingredient.

The compound represented by Chemical Formula 1 above, pharmaceutically acceptable salt thereof, prevention, and treatment are as described above.

As used herein, the term "active ingredient" refers to an ingredient that exhibits the desired activity by itself or an ingredient which can exhibit the desired activity together with a carrier which itself has no activity, etc.

As used herein, the term "prevention" refers to all actions to inhibit or delay occurrence, spread or recurrence of cancer-related diseases by administration of the composition of the present disclosure, and the term "treatment" refers to all actions to improve or beneficially change the symptoms of the above diseases by administration of the composition of the present disclosure.

Specifically, the pharmaceutical composition of the present disclosure can prevent or treat cancer-related diseases by inhibiting the activity of signal transducers and activators of transcription 3 (STAT3), but is not limited thereto.

As used herein, the term "STAT3" is a transcriptional regulatory factor that regulates the expressions of genes involved in cell growth, differentiation, and apoptosis, etc., via intracellular signal transduction in relation to various cytokines and growth factors. STAT3 is known to contribute to the malignancy of cancer cells through overexpression and abnormal activation in various cancer cells (H. Q. Wang. et al., *MedChem.* 3, e124, 2022). In addition, it is known that when STAT3 is activated, it regulates the functions of various immune cells such as natural killer cells in the tumor microenvironment, thereby weakening anticancer immune effects (J. Huynh, *Nature Rev. Cancer.* 19, 82, 2019).

Specifically, the pharmaceutical composition of the present disclosure can prevent or treat cancer-related diseases by inhibiting the activity of STAT3 and controlling the activity of natural killer cells or bone marrow-derived macrophages, which are immune cells, but is not limited thereto.

In one embodiment of the present disclosure, it was confirmed that the novel compounds of the present disclosure inhibited the phosphorylation of STAT3 in cancer cells, inhibited the growth of cancer cells, inhibited the expression of STAT3 target genes and apoptotic genes, induced cancer cell apoptosis by decomposing apoptosis marker proteins, and inhibited STAT3 activity even in natural killer cells and bone marrow-derived macrophages. As a result, it was confirmed that the novel compounds of the present disclosure exhibited the effects of inhibiting the growth of cancer cells and increasing the activity of immune cells in the tumor microenvironment by inhibiting STAT3 activity.

Specifically, cancer that may be prevented or treated by the pharmaceutical composition of the present disclosure may be any one selected from the group consisting of colorectal cancer, pancreatic cancer, gastric cancer, liver cancer, breast cancer, cervical cancer, thyroid cancer, parathyroid cancer, lung cancer, non-small cell lung cancer, prostate cancer, gallbladder cancer, bile duct cancer, non-Hodgkin's lymphoma, Hodgkin's lymphoma, blood cancer, bladder cancer, renal cancer, ovarian cancer, melanoma, colon cancer, bone cancer, skin cancer, head cancer, uterine cancer, rectal cancer, brain tumor, anal cancer, fallopian tube carcinoma, endometrial carcinoma, vaginal cancer, vulva carcinoma, esophageal cancer, small intestine cancer, endocrine cancer, adrenal cancer, soft tissue sarcoma, urethral cancer, penis cancer, ureter cancer, renal cell carcinoma, renal pelvic carcinoma, central nervous system tumor, primary central nervous system lymphoma, spinal cord tumor, brainstem glioma, and pituitary adenoma, but is not limited thereto.

Specifically, the pharmaceutical composition according to the present disclosure may contain the compound represented by Chemical Formula 1 or a pharmaceutically acceptable salt thereof as an active ingredient in an amount of 0.0001% to 99.9% by weight, specifically 0.01% to 80% by weight, and more preferably 1% to 10% by weight based on the total weight of the composition, but is not limited thereto.

The composition of the present disclosure may further include a pharmaceutically acceptable carrier, a diluent, or an excipient, and may be prepared into various formulations including oral formulation such as a powder, a granule, a tablet, a capsule, a suspension, an emulsion, a syrup, an aerosol, etc., and an injection of sterile injectable solution, etc. according to conventional methods depending on the desired purpose. Additionally, the composition may be administered through various routes including oral administration or intravenous, intraperitoneal, subcutaneous, rectal, topical administration, etc. Examples of the appropriate carriers, excipients, and diluents that may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and minerals. Further, the composition of the present disclosure may further include a filler, an anti-coagulant, a lubricant, a wetting agent, a flavoring agent, an emulsifier, a preservative, etc.

Examples of a solid formulation for oral administration include a tablet, a pill, a powder, a granule, a capsule, etc. These solid formulations are prepared by mixing the composition with at least one excipient, for example, starch, calcium carbonate, sucrose, lactose, gelatin, etc. Further, a lubricant such as magnesium stearate or talc may be also used in addition to the simple excipient.

Examples of a liquid formulation for oral administration include a suspension, a solution for internal use, an emulsion, a syrup, etc. The liquid formulation may include, in addition to water, a commonly available simple diluent, or liquid paraffin, various excipients, such as a wetting agent, a sweetener, an aromatic, a preservative, etc.

A formulation for parenteral administration may include a sterilized aqueous solution, a non-aqueous solvent, a suspension, an emulsion, a lyophilized formulation, and a suppository. As the non-aqueous solvent and the suspension, propylene glycol, polyethylene glycol, a vegetable oil such as olive oil, or an injectable ester such as ethyl oleate may be used. As a base for the suppository formulation, witepsol, macrogol, tween61, cacao butter, laurin butter, glycerogelatin, etc. may be used. Meanwhile, the injection may include conventional additives such as a solubilizer, an isotonic agent, a suspension, an emulsifier, a stabilizer, a preservative, etc.

The composition of the present disclosure may be administered in a pharmaceutically effective amount. As used herein, the term "pharmaceutically effective amount" refers to an amount sufficient to treat a disease at a reasonable benefit/risk ratio applicable to any medical treatment without causing an adverse effect, and the effective dosage level may be determined based on the factors including the heath condition of a patient, the type and severity of a disease, the activity of a drug, the sensitivity to a drug, an administration method, an administration time, an administration route and an excretion rate, a duration of treatment, drugs used simultaneously or in combination, and other factors well known in the medical field. The composition may be administered as an individual therapeutic agent or in combination with other therapeutic agents, and may be administered sequentially or simultaneously with conventional therapeutic agent, or may be subjected to single or multiple administration. In view of all the above elements, it is important to administer the composition at a dose in which the maximum effect can be achieved with the minimum amount without adverse effects. Thus, the dose of the composition may be easily determined by those skilled in the art.

For example, the dose may increase or decrease depending on the route of administration, severity of disease, gender, weight, age, etc., and thus, the above dose does not limit the scope of the present disclosure in any way.

Specifically, the pharmaceutical composition of the present disclosure may be, for example, administered at a dose of 1 mg/kg to 10 mg/kg of body weight per day to animals, including humans, but is not limited thereto. The frequency of administration of the composition of the present disclosure is not particularly limited, but may be administered once a day or divided into multiple doses. However, the dose may increase or decrease depending on the route of administration, severity of disease, gender, weight, age, etc., and thus, the above dose does not limit the scope of the present disclosure in any way.

Specifically, the pharmaceutical composition of the present disclosure may further include an anticancer agent, but is not limited thereto.

More specifically, the anticancer agent may be any one selected from the group consisting of DNA alkylating agents, anticancer antibiotics, plant alkaloids, targeted anticancer agents, and cancer immunotherapy, but is not limited thereto.

Even more specifically, the anticancer agent may be any one selected from the group consisting of mechlorethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin C, bleomycin, vincristine, vinblastine, paclitaxel, docetaxel, etoposide, teniposide, topotecan, irinotecan, Glivec, Tasigna, Herceptin, Iressa, Nexavar, Yervoy, Opdivo, Keytruda, Atezol, Tecentriq, and Bavencio, but is not limited thereto.

There are many causes of anticancer drug resistance, and among them, the tumor microenvironment has recently become a subject of interest. Tumors themselves have very complex heterogeneity and interact with a wide variety of cells around them, and this is collectively referred to as the tumor microenvironment (TME). The tumor microenvironment includes not only tumor cells but also normal epithelial cells, endothelial cells, fibroblasts, and immune cells. These cells are organically connected to each other and are closely related to anticancer drug resistance (M. R. Junttila, *Nature* 501, 346, 2013). For example, important immune cells in the tumor microenvironment include regulatory T cells (Treg), myeloid-derived suppressor cells (MDSC), cancer-associated fibroblasts (CAF), and natural killer cells (NK cells), etc.

In this regard, it is known that when STAT3 is activated, it regulates the functions of various immune cells such as natural killer cells in the tumor microenvironment, thereby weakening anticancer immune effects (J. Huynh, *Nature Rev. Cancer,* 19, 82, 2019).

Since the novel compounds of the present disclosure or pharmaceutically acceptable salts thereof exhibits the effects of inhibiting the growth of cancer cells and increasing the activity of immune cells in the tumor microenvironment by inhibiting STAT3 activity, it can be effectively used as a drug that overcomes the resistance of anticancer drugs and increases drug activity by activating anticancer immunity, which converts the tumor microenvironment from a cold cancer that does not respond to cancer immunotherapy to a hot cancer that responds to cancer immunotherapy.

Still another aspect of the present disclosure provides a method for preventing or treating cancer: including administering a pharmaceutical composition containing a compound represented by Chemical Formula 1 above, or a pharmaceutically acceptable salt thereof, as an active ingredient, into a subject.

The compound represented by Chemical Formula 1 above, pharmaceutically acceptable salt thereof, active ingredient, pharmaceutical composition, cancer, prevention and treatment are as described above.

As used herein, the term "subject" may mean all animals such as cattle, horses, sheep, pigs, goats, camels, antelopes, dogs, cats, human, etc., which have or are likely to develop cancer, but is not limited thereto.

The prevention or treatment method of the present disclosure may specifically include the step of administering the composition in a pharmaceutically effective amount to a subject who has or is likely to develop cancer.

As used herein, the term "administration" means introducing the composition of the present disclosure to a subject who exhibits or is likely to develop symptoms of cancer and related diseases by any suitable method, and the composition of the present disclosure can be administered through various routes, such as oral or parenteral, as long as it can reach a desired tissue.

Specifically, the composition of the present disclosure may be administered via an intraperitoneal route, an intravenous route, an intramuscular route, a subcutaneous route, an intradermal route, an oral route, an intranasal route, an intrapulmonary route or an intrarectal route, etc., according to the purpose, but is not particularly limited thereto.

Specifically, the pharmaceutical composition of the present disclosure may be, for example, administered at a dose of 1 mg/kg to 10 mg/kg of body weight per day to animals, including humans, but is not limited thereto. The frequency of administration of the composition of the present disclosure is not particularly limited, but may be administered once a day or divided into multiple doses. However, the dose may increase or decrease depending on the route of administration, severity of disease, gender, weight, age, etc., and thus, the above dose does not limit the scope of the present disclosure in any way.

Specifically, the pharmaceutical composition can prevent or treat cancer-related diseases by inhibiting the activity of signal transducers and activators of transcription 3 (STAT3), but is not limited thereto.

Even another aspect of the present disclosure provides a food composition for preventing or improving cancer, including a compound represented by Chemical Formula 1 above, or a sitologically acceptable salt thereof, as an active ingredient.

The compound represented by Chemical Formula 1 above, active ingredient, cancer, and prevention are as described above.

As used herein, the term "sitologically acceptable salt" is as defined in the term "pharmaceutically acceptable salt".

As used herein, the term "improvement" may refer to all actions that at least reduce a parameter related to the condition to be treated, for example, the degree of symptom, by administration of the composition according to the present disclosure.

As used herein, the term "food" may include all foods in a conventional sense, such as meats, sausages, breads, chocolates, candies, snacks, cookies, pizzas, ramens, other noodles, gums, dairy products including ice cream, various kinds of soups, beverages, teas, drinks, alcoholic beverages, vitamin complexes, health functional foods, and health foods, etc.

The food composition of the present disclosure can be taken easily as daily food, and thus may be expected to have great cancer-improving effects, and accordingly, it can be very effectively used for the purpose of promoting health.

In addition, the food composition of the present disclosure may be used as a health functional food. As used herein, the term "health functional food" refers to a food which is prepared and processed with raw materials or components having functionality useful for a human body in accordance with the Health Functional Food Act. In particular, the term "functionality" refers to the ingestion for the purpose of controlling nutrients for the structure and function of the human body or obtaining useful effects for hygienic purposes, such as physiological effects, etc. The food of the present disclosure may be prepared according to a method commonly employed in the art, and raw materials and ingredients commonly used in the art may be added when preparing the food. Additionally, the formulation of the food is not limited so long as it is recognized as a food. The food composition of the present disclosure may be prepared in various formulations, and the food composition of the present disclosure uses a food as a raw material unlike general drugs, and thus has no side effects that may occur during long-term administration of the drugs, is highly portable, and may be administered as an adjuvant for enhancing anticancer effects.

The health food refers to a food that has an active health maintenance or promotion effect compared to general food, and a health supplement food refers to a food intended for health supplement. In some cases, the terms health functional food, health food, and health supplement food are used interchangeably.

Specifically, the health functional food is a food prepared by adding the extract of the present disclosure to food materials such as beverages, teas, spices, gum, and confectionery, etc., or a food prepared by means of encapsulation, powdering, or suspension. When the health functional food is ingested, a specific health effect may be obtained. However, unlike general drugs, since the health functional food uses food as a raw material, there is an advantage in that there are no side effects that may occur during long-term administration of the drugs.

The food composition may further include a physiologically acceptable carrier, and the type of carrier is not particularly limited, and any carrier commonly used in the art may be used.

Additionally, the food composition may contain additional ingredients that are conventionally used in food compositions so as to improve smell, taste, vision, etc. For example, the composition may contain vitamins A, C, D, E, B1, B2, B6, and B12, niacin, biotin, folate, pantothenic acid, etc. In addition, the food composition may contain minerals such as zinc (Zn), iron (Fe), calcium (Ca), chromium (Cr), magnesium (Mg), manganese (Mn), copper (Cu), and chromium (Cr), etc. Further, the food composition may contain amino acids such as lysine, tryptophan, cysteine, valine, etc.

Additionally, the food composition may also contain food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclamate, saccharin, sodium, etc.), flavors (vanillin, lactones, etc.), swelling agents (alum, potassium D-hydrogen tartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

The food composition of the present disclosure may include conventional food additives, and the conformity of the "food additive" is determined, as long as there are no other regulations, by a standard or criterion regarding the relevant article according to general provisions of the Korean Food Additives Codex and General Test Method approved by the Korean Ministry of Food and Drug Safety (MFDS).

Items listed on the "Korean Food Additives Codex" may include, for example, a chemical composite such as ketone, glycine, potassium citrate, nicotinic acid, cinnamic acid, etc., natural additives such as persimmon color, *Glycyrrhiza* extract, crystalline cellulose, Kaoliang color, guar gum, etc., and mixed preparations such as L-glutamic acid sodium agent, alkali agents for noodles, preservative formulation, tar color formulation, etc.

The food composition of the present disclosure may include the compound of Chemical Formula 1 or a sitologically acceptable salt thereof in an amount of 0.01% to 95% by weight, preferably 1% to 80% by weight, based on the total weight of the composition. In addition, the compound of Chemical Formula 1 or a sitologically acceptable salt thereof contained in the food composition of the present disclosure may be obtained by the same or similar method as the extraction method mentioned in the preparation of the pharmaceutical composition, but is not limited thereto.

Additionally, the food composition of the present disclosure can be prepared and process in the form of tablets, capsules, powders, granules, liquids, pills, etc. for the purpose of preventing or improving cancer.

For example, the health functional food in the form of tablet may be prepared as follow: a mixture of the compound of Chemical Formula 1 or a sitologically acceptable salt, an excipient, a binder, a disintegrant, etc., and other additives can be granulated using a conventional method, and then compression molding process is performed with a lubricant. Alternatively, the mixture can be directly subjected to the compression molding process. In addition, the health formulated food in the form of tablet may include a sweetening agent, if necessary, and it can be coated with a coating material, if necessary.

In the case of health functional food in the form of capsule, a hard capsule can be prepared by filling a mixture of additives such as the compound of Chemical Formula 1 or a sitologically acceptable salt thereof and an excipient, etc., or granules thereof or coated granules into a conventional hard capsule, and a soft capsule can be prepared by filling a mixture of additives such as the guanine derivative or a sitologically acceptable salt thereof and an excipient, etc. into a capsule base such as gelatin, etc. The soft capsule can contain a plasticizer such as glycerin or sorbitol, etc., a coloring agent, a preservative, etc., if necessary.

The health functional food in the form of bolus can be prepared by molding a mixture of the compound of Chemical Formula 1 or a sitologically acceptable salt thereof, an excipient, a binder, and a disintegrant, etc. by a suitable method, and can be coated with white sugar or other coating materials, or covered with starch, talc, or proper materials.

The health functional food in the form of granule can be produced by granulating a mixture of the compound of Chemical Formula 1 or a sitologically acceptable salt thereof, an excipient, a binder, and a disintegrant, etc. by a suitable method. When needed, it can include a flavoring agent, a sweetening agent, etc. When the health functional food in the form of granule is subjected to a particle size test with No. 12 (1680 μm), No. 14 (1410 μm) and No. 45 (350 μm) sieves, all particles may pass through the No. 12 sieve, the residual amount may be no more than 5.0% with the No. 14 sieve, and the amount of particles passing through the No. 45 sieve may be no more than 15.0% based on the total amount thereof.

The definition of terms such as the excipient, binder, disintegrant, lubricant, sweetening agent, flavoring agent, etc. is described in literature known in the art and may encompass those with the same or similar functions (*The Korean Pharmacopoeia review*, Moonsungsa Publication Co., Korea Pharmaceutical University Association, 5th Ed., pp. 33-48, 1989).

Yet another aspect of the present disclosure provides a feed composition for preventing or improving cancer, including a compound represented by Chemical Formula 1 above, or a sitologically acceptable salt thereof, as an active ingredient.

The compound represented by Chemical Formula 1 above, sitologically acceptable salt thereof, active ingredient, cancer, and prevention, and improvement are as described above.

As used herein, the term "feed" refers to food ingested by an animal, and specifically, it may refer to a material that supplies organic or inorganic nutrients necessary to maintain the life of the animal or to produce meat, milk, etc. The feed may include feed additives and may be prepared in various forms known in the art.

A composition including the compound of Chemical Formula 1 of the present disclosure or a sitologically acceptable salt thereof may be used to prevent or treat occurrence of cancer in subjects other than humans such as livestock or companion animals, and may be used as a functional feed additive or a feed composition.

An amount of the compound of Chemical Formula 1 or a sitologically acceptable salt thereof in the feed composition according to the present disclosure may be appropriately adjusted according to the type and age of the livestock to be treated, application form, desired effects, etc., for example, in the range of 1% to 99% by weight, preferably 10% to 90% by weight, more preferably 20% to 80% by weight, but is not limited thereto.

The type of the feed is not particularly limited, and a feed conventionally used in the corresponding technical field may be used. Non-limiting examples of the feed include vegetable feeds such as grains, root plants, food-processing by-products, algae, fibers, fat and oils, starches, Cucurbitaceae vegetables, or grain by-products; and animal feeds such as proteins, inorganic substances, fats and oils, minerals, single-cell proteins, animal plankton, or foods. These feeds may be used alone or in a combination of at least two thereof.

Additionally, the compound of the present disclosure or a sitologically acceptable salt thereof may be used as a feed additive added to a feed composition. The feed additive may be used to improve productivity or health of a target animal, but is not limited thereto. The feed additive may correspond to a supplementary feed under the Control of Livestock and Fish Feed Act.

The feed additive of the present disclosure may be used by further mixing one or more ingredients of organic acids such as citric acid, fumaric acid, adipic acid, lactic acid, etc. and natural antioxidants such as polyphenols, catechins, tocopherols, vitamin C, green tea extract, chitosan, tannic acid, etc., and depending on needs, other conventional additives such as buffers, bacteriostatic agents, etc. may be added. In addition, it may be formulated into a liquid, capsule, granule, or tablet as needed.

The feed or feed additive may further include substances exhibiting various effects such as supplementation of nutrients and prevention of weight loss, enhancement of digestive availability of fibers in the feed, improvement of oil quality, prevention of reproductive disorders and improvement in conception rates, prevention of high-temperature stress in summer, etc. For example, it may be used together with nutritional supplements, growth promoters, digestive absorption accelerators, and prophylactic agents, in addition to the main components such as various supplements such as amino acids, inorganic salts, vitamins, antioxidants, antifungal and microbial preparations, etc., vegetable protein feeds such as milled or crushed wheat, barley, corn, etc., animal protein feeds such as powdered blood, powdered meat, powdered fish, etc., animal fats and vegetable fats.

The feed and feed additive of the present disclosure may be fed to a number of animals, including mammals and poultry. For example, in order to maintain or improve beauty, these can be used in livestock, such as cattle, goats, etc.; and pets such as dogs and cats, etc., but are not limited thereto.

Further another aspect of the present disclosure provides the use of a composition including a compound represented by Chemical Formula 1 above, or a pharmaceutically acceptable salt thereof, as an active ingredient for preventing or treating cancer.

The compound represented by Chemical Formula 1, pharmaceutically acceptable salt thereof, active ingredient, cancer, prevention and treatment are as described above.

MODE FOR CARRYING OUT THE INVENTION

The present disclosure will be described in detail by way of Examples. However, these Examples are given for illustrative purposes only, and the scope of the invention is not intended to be limited by these Examples.

Synthesis Example 1: Synthesis of CG133

Among the compounds of Chemical Formula 1, CG133 was synthesized using the method shown in Reaction Scheme 1 below:

[Reaction Scheme 1]

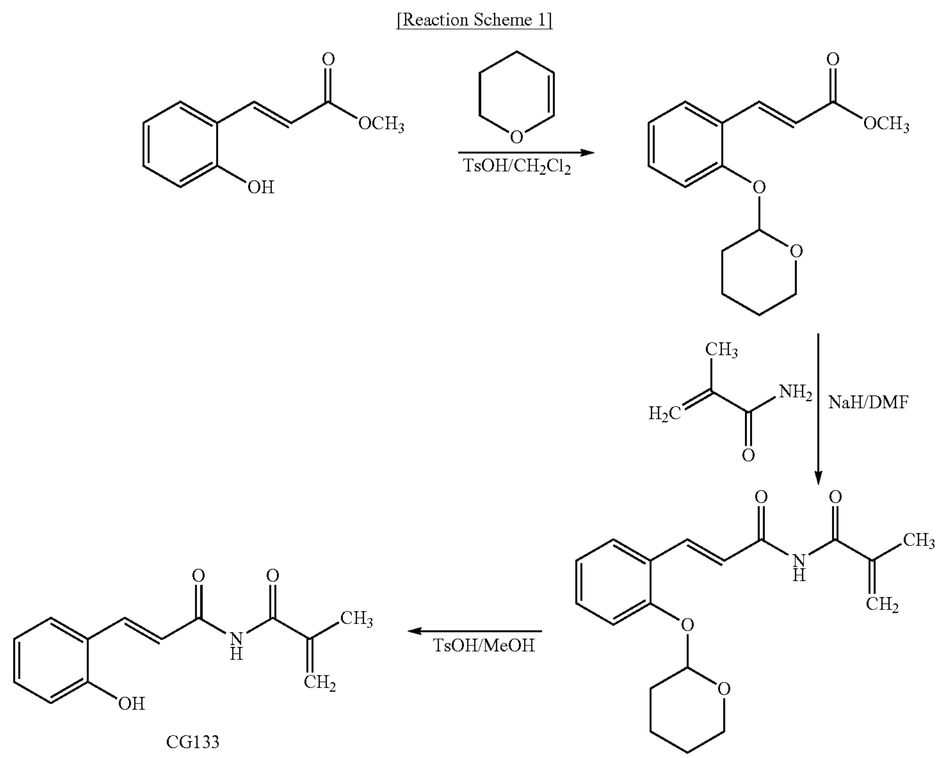

CG133

Specifically, methyl 2-hydroxycinnamate (5 g) was dissolved in methylene chloride (200 mL), and then 3,4-dihydropyran (2.6 g, 1.1 equivalents) was added thereto. A small amount of p-toluene sulfonic acid (5-10 mg) was added to the reaction solution and stirred at room temperature for 4 hours. The reaction was terminated by adding a small amount of triethyl amine (0.5 mL), and the solvent was concentrated under reduced pressure and extracted three times using ethyl acetate (EA) and water. Thereafter, the organic layer was dried over $MgSO_4$, filtered, and concentrated under reduced pressure. The concentrate was used in the next reaction without purification.

After dissolving the concentrate and methacrylamide (2.7 g, 1.1 equivalents) in DMF (N,N-dimethylformamide, 100 mL), sodium hydride (800 mg, 1.2 equivalents) was added to the mixed solution and stirred at room temperature for 7 hours. The reaction was terminated by adding 50 mL of saturated ammonium chloride solution and water, and then extracted three times using ethyl acetate and water. Thereafter, the organic layer was dried over $MgSO_4$, filtered, and concentrated under reduced pressure. The concentrate was dissolved in 100 ml of methyl alcohol, p-toluene sulfonic acid (20 mg) was added thereto, and the mixture was stirred at room temperature for 4 hours. Then, the solvent was concentrated under reduced pressure and extracted three times using ethyl acetate (EA) and water. Thereafter, the organic layer was dried over $MgSO_4$, filtered, and concentrated under reduced pressure. The concentrate was purified using column chromatography (EA:hexane=20:80) to obtain compound CG133 (3.1 g, 47.7%, light yellow powder).

The m.p. of compound CG133 is 198° C., and the $^1$H- and $^{13}$C-NMR analysis results are as follows:

$^1$H-NMR (400 MHZ, $CDCl_3$) δ 9.38 (brs, 1H), 9.30 (brs, 1H), 7.85 (d, J=16 Hz, 1H), 7.29 (d, J=16 Hz, 1H), 7.25 (d, J=7.6 Hz, 1H), 6.93 (t, J=7.6 Hz, 1H), 6.65 (d, J=7.6 Hz, 1H), 6.57 (t, J=7.6 Hz, 1H), 5.67 (s, 1H), 5.35 (s, 1H), 1.74 (s, 3H);

$^{13}$C-NMR (100 MHz, $CDCl_3$) δ 167.08, 166.96, 156.55, 140.48, 139.26, 130.86, 128.32, 121.82, 121.21, 119.02, 118.85, 115.87, 17.93.

Synthesis Example 2: Synthesis of CG164

Among the compounds of Chemical Formula 1, CG164 was synthesized using the method shown in Reaction Scheme 2 below:

[Reaction Scheme 2]

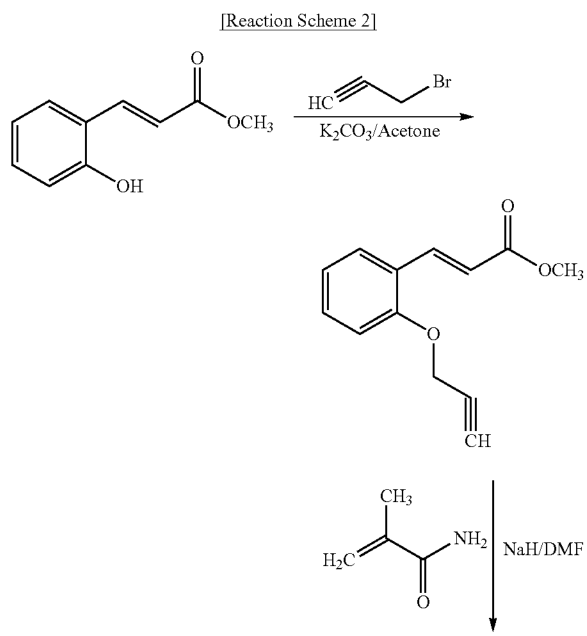

-continued

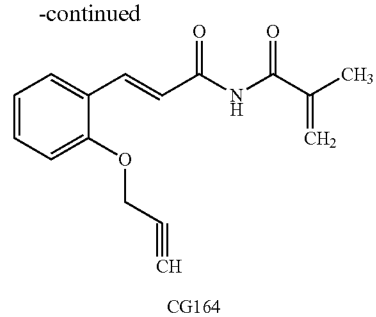

CG164

Specifically, methyl 2-hydroxycinnamate (5 g) was dissolved in acetone (200 mL), and potassium carbonate (4.7 g, 1.2 equivalents) was added to the solution. Propargyl bromide (4.0 g, 1.2 equivalents) was added to the reaction solution, the solution was maintained at 50-60° C. while stirring for 6 hours. When the reaction was completed, the reaction solution was stirred at room temperature for 1 hour, filtered, and concentrated under reduced pressure. The concentrate was used in the next reaction without purification.

After dissolving the concentrate and methacrylamide (2.7 g, 1.1 equivalents) in DMF (N,N-dimethylformamide, 100 mL), sodium hydride (800 mg, 1.2 equivalents) was added to the mixed solution and stirred at room temperature for 7 hours. The reaction was terminated by adding 50 ml of saturated ammonium chloride solution and water, and then extracted three times using ethyl acetate and water. Thereafter, the organic layer was dried over $MgSO_4$, filtered, and concentrated under reduced pressure. The concentrate was purified using column chromatography (EA:hexane=15:85) to obtain compound CG164 (3.8 g, 50.4%, white powder).

The m.p. of compound CG164 is 122° C., and the $^1$H- and $^{13}$C-NMR analysis results are as follows:

$^1$H-NMR (600 MHZ, $CDCl_3$) δ 8.32 (brs, 1H), 8.25 (d, J=16 Hz, 1H), 7.76 (d, J=16 Hz, 1H), 7.71 (dd, J=1.8, 7.8 Hz, 1H), 7.40 (t, J=7.8 Hz, 1H), 7.08 (d, J=7.6 Hz, 1H), 7.04 (t, J=7.8 Hz, 1H), 5.89 (s, 1H), 5.65 (s, 1H), 4.81 (d, J=2.4 Hz, 2H), 2.53 (t, J=2.4 Hz, 1H), 2.05 (s, 3H);

$^{13}$C-NMR (150 MHz, $CDCl_3$) δ 167.61, 166.60, 156.45, 141.31, 139.93, 131.74, 128.92, 124.26, 122.50, 121.68, 119.73, 112.79, 78.19, 76.01, 56.17, 18.46.

Synthesis Example 3: Synthesis of CG165

Among the compounds of Chemical Formula 1, CG165 was synthesized by the following method.

Specifically, a compound was synthesized by reacting CG164 synthesized in Synthesis Example 2 with methyl iodide in acetone in the presence of potassium carbonate ($K_2CO_3$), which was named CG165, and the $^1$H-NMR data thereof is shown in FIG. 1.

The m.p. of compound CG165 is 115° C., and the $^1$H- and $^{13}$C-NMR analysis results are as follows:

$^1$H-NMR (600 MHZ, $CDCl_3$) δ 7.87 (d, J=15.6 Hz, 1H), 7.47 (dd, J=1.8 Hz, 7.8 Hz, 1H), 7.35 (dt, J=1.8 Hz, 7.8 Hz, 1H), 7.04 (d, J=7.8 Hz, 1H), 7.01 (t, J=7.8 Hz, 1H), 6.86 (d, J=15.6 Hz, 1H), 5.43 (m, 2H), 4.77 (d, J=2.4 Hz, 2H), 3.30 (s, 3H), 2.53 (t, J=2.4 Hz, 1H), 2.06 (d, J=1.2 Hz, 3H);

$^{13}$C-NMR (150 MHz, $CDCl_3$) δ 174.85, 170.07, 156.40, 142.26, 138.41, 131.30, 129.52, 124.15, 122.34, 121.82, 121.71, 112.73, 78.06, 76.07, 56.09, 32.62, 19.05.

Synthesis Example 4: Synthesis of CG126

Among the compounds of Chemical Formula 1, CG126 was synthesized by the following method.

Specifically, CG126 was synthesized in the same manner as in Reaction Scheme 2 above, using 2-methoxycinnamic acid as a starting material.

The m.p. of compound CG126 is 126° C., and the $^{1}$H- and $^{13}$C-NMR analysis results are as follows:

$^{1}$H-NMR (500 MHZ, $CDCl_3$) δ 8.22 (d, J=15.5 Hz, 1H), 8.20 (brs, 1H), 7.75 (d, J=15.5 Hz, 1H), 7.64 (dd, J=1.5 Hz, 7.5 Hz, 1H), 7.36 (dt, J=1.5 Hz, 7.7 Hz, 1H), 6.96 (t, J=7.5 Hz, 1H), 6.92 (d, J=8.0 Hz, 1H), 5.85 (s, 1H), 5.62 (m, 1H), 3.90 (s, 3H), 2.03 (s, 3H);

$^{13}$C-NMR (100 MHZ, $CDCl_3$) δ 167.61, 166.47, 158.66, 141.87, 140.00, 131.96, 129.12, 123.60, 122.34, 120.68, 119.32, 111.14, 55.53, 18.45.

Synthesis Example 5: Synthesis of CG127

Among the compounds of Chemical Formula 1, CG127 was synthesized by the following method.

Specifically, CG127 was synthesized in the same manner as in Reaction Scheme 2 above, using 2-methylcinnamaic acid as a starting material.

The m.p. of compound CG127 is 135° C., and the $^{1}$H- and $^{13}$C-NMR analysis results are as follows:

$^{1}$H-NMR (500 MHZ, $CDCl_3$) δ 8.21 (brs, 1H), 8.18 (d, J=16 Hz, 1H), 7.69 (d, J=7.5 Hz, 1H), 7.66 (d, J=15.5 Hz, 1H), 7.29 (dt, J=1.5 Hz, 7.5 Hz, 1H), 7.23 (m, 2H), 5.87 (s, 1H), 5.64 (m, 1H), 2.47 (s, 3H), 2.04 (s, 3H);

$^{13}$C-NMR (100 MHZ, $CDCl_3$) δ 167.32, 166.46, 144.16, 139.87, 138.18, 133.47, 130.81, 130.44, 127.00, 126.35, 122.57, 120.08, 18.85, 18.42.

Synthesis Example 6: Synthesis of CG155

Among the compounds of Chemical Formula 1, CG155 was synthesized by the following method.

Specifically, CG155 was synthesized by reacting CG133 prepared in Synthesis Example 1 with 4-(bromomethyl) pyridine in the presence of sodium hydride.

The m.p. of compound CG155 is 156° C., and the $^{1}$H- and $^{13}$C-NMR analysis results are as follows:

$^{1}$H-NMR (600 MHZ, $CDCl_3$) δ 8.65 (s, 2H), 8.44 (brs, 1H), 8.30 (d. J=15.6 Hz. 1H), 7.82 (d, J=15.6 Hz, 1H), 7.71 (dd, J=1.2 Hz, 7.8 Hz, 1H), 7.41 (d, J=4.8 Hz, 2H), 7.34 (dt, J=1.2 Hz, 8.4 Hz, 1H), 7.03 (t, J=7.8 Hz, 1H), 6.89 (d, J=7.8 Hz, 1H), 5.90 (s, 1H), 5.65 (d, J=1.2 Hz, 1H), 5.21 (s, 2H), 2.05 (s, 3H);

$^{13}$C-NMR (150 MHz, $CDCl_3$) δ 176.66, 166.55, 156.97, 150.02, 145.74, 141.18, 139.88, 131.89, 129.42, 124.13, 122.59, 121.61, 121.56, 120.11, 112.46, 68.63, 18.45.

Synthesis Example 7: Synthesis of CG168

Among the compounds of Chemical Formula 1, CG168 was synthesized by the following method.

Specifically, CG168 was synthesized in the same manner as in Reaction Scheme 2 above, using 2-chlorocinnamaic acid as a starting material.

The m.p. of compound CG168 is 147° C., and the $^{1}$H- and $^{13}$C-NMR analysis results are as follows:

$^{1}$H-NMR (600 MHZ, $CDCl_3$) δ 8.55 (brs, 1H), 8.29 (d, J=16.2 Hz, 1H), 7.79 (dd, J=1.2 Hz, 7.8 Hz, 1H), 7.76 (d, J=15.6 Hz, 1H), 7.44 (d, J=7.8 Hz, 1H), 7.31 (m, 2H), 5.94 (s, 1H), 5.69 (d, J=1.2 Hz, 1H), 2.06 (s, 3H);

$^{13}$C-NMR (150 MHz, $CDCl_3$) δ 167.12, 166.71, 141.98, 139.68, 135.40, 132.84, 131.35, 130.16, 128.11, 127.08, 122.94, 121.79, 18.45.

Synthesis Example 8: Synthesis of CG187

Among the compounds of Chemical Formula 1, CG187 was synthesized by the following method.

Specifically, CG187 was synthesized in the same manner as in Reaction Scheme 2 above, using 2-hydroxycinnamic acid as a starting material.

The m.p. of compound CG187 is 127° C., and the $^{1}$H- and $^{13}$C-NMR analysis results are as follows:

$^{1}$H-NMR (600 MHZ, $CDCl_3$) δ 8.43 (brs, 1H). 8.31 (d, J=15.6 Hz, 1H), 7.76 (d. J=16.2 Hz, 1H), 7.70 (dd, J=1.2 Hz, 7.8 Hz, 1H), 7.5-7.3 (m, 6H), 6.98 (m, 2H), 5.89 (s, 1H), 5.62 (d, J=1.2 Hz, 1H), 5.20 (s, 2H), 2.04 (s, 3H);

$^{13}$C-NMR (100 MHz, $CDCl_3$) δ 167.70, 166.55, 157.65, 141.56, 139.90, 136.59, 131.89, 120.01, 128.69, 128.64, 127.99, 127.77, 127.36, 124.06 122.47, 121.07, 121.04, 119.63, 112.73, 70.42, 18.45.

Experiential Example 1: Cell Cultivation

All cell lines used to verify the in vitro activity of the compounds prepared in Synthesis Examples 1 to 8 were purchased from ATCC (Manassas, VA, USA). Prostate cancer cell line DU-145, breast cancer cell line MDA-MB-468, lung cancer cell line HCC827 and human foreskin fibroblast HFF were cultured in RPMI-1640 (Gibco, Gaithersburg, MD, USA) medium supplemented with 10% FBS (Gibco) and 100 U/mL penicillin. MCF10A, human breast epithelial cells, were cultured in DMEM-F12 (Gibco) medium supplemented with 10% fetal bovine serum (FBS), 0.5% penicillin/streptomycin, EGF (20 ng/ml), insulin (10 μg/mL), and hydrocortisone (0.5 mg/mL). Natural killer cell NKL cell line was cultured in RPMI-1640 (ATCC, 30-2001) medium supplemented with 10% FBS (Gibco) and 50 ng/ml hIL-2 (Peprotech, East Windsor, NJ, USA). All cell lines used in the experiment were maintained in a 5% $CO_2$ incubator.

Experiential Example 2: Western Blot Analysis

Prostate cancer cell line DU-145, breast cancer cell MDA-MB 468, lung cancer cell HCC827, natural killer cells (NKL), or bone marrow-derived macrophages (BMDM) ($4\times10^5$ cells), which are immune cells, were plated in a 6-well plate. After 24 hours, the cells were each treated with 0.1% DMSO, HCA, EA, and the compounds prepared in Synthesis Examples 1 to 8 according to concentration and time, washed with PBS, and recovered using RIPA buffer. 20 g of protein quantified using the Bio-Rad protein assay kit (Bio-Rad, Hercules, California, USA) was subjected to 8% SDS-PAGE electrophoresis and transferred to a PVDF membrane (EMD Millipore, Billerica, MA, USA). After blocking the membrane with TBST containing 5% skim milk, the experiment was performed using primary and secondary antibodies. The primary antibodies used were p-STAT3 (Y705) (Cell Signaling), STAT3 (Cell Signaling), Cyclin D1 (Santa Cruz), Cyclin A (Santa Cruz), Mcl-1 (Santa Cruz), Survivin (Cell Signaling), Bcl-XL (Santa Cruz), and PARP (Cell Signaling) GAPDH (Santa Cruz), and the secondary antibodies used were HRP-conjugated goat anti-rabbit and anti-mouse IgG (Jackson ImmunoResearch Laboratories, West Grove, PA, USA). The antibodies used were each washed three times with TBST, and bands were detected using Luminata Forte Western HRP substrate (EMD Millipore) by LAS 4000 mini (GE Healthcare Life Sciences). Subsequently, correction using GAPDH was performed using the MultiGauge program (Fuji Photo Film, Tokyo, Japan).

Example 1: Confirmation of STAT3 Phosphorylation Inhibitory Effect in Cancer Cell Lines—1

The STAT3 phosphorylation inhibitory effect of the cinnamamide derivatives of Chemical Formula 1 prepared in Synthesis Examples 1 to 8 in cancer cell lines was confirmed by Western blot.

Specifically, the STAT3 phosphorylation inhibitory effect in rectal cancer cell was confirmed line as an example of representative carcinoma. The results are shown in Table 2 below.

TABLE 2

| Name of Compounds | Compound Structure | Concentration at which STAT3 activity (p-STAT3) is inhibited by 50% (μM; $IC_{50}$) |
|---|---|---|
| CG126 | 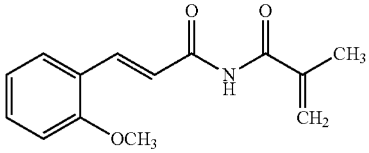 [SMILES: C=C(C)C(=O)NC(=O)/C=C/c1ccccc1OC] | 3.7 |
| CG127 | 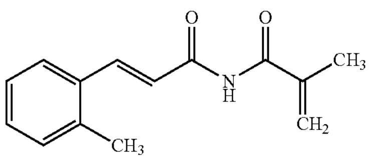 [SMILES: C=C(C)C(=O)NC(=O)/C=C/c1ccccc1C] | 8.1 |
| CG133 | 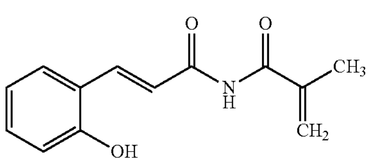 [SMILES: C=C(C)C(=O)NC(=O)/C=C/c1ccccc1O] | 6.2 |
| CG155 | 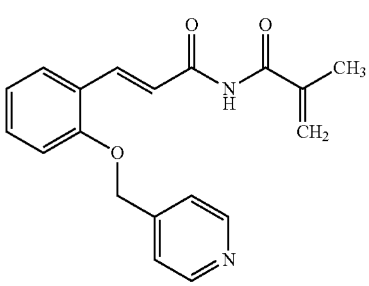 [SMILES: C=C(C)C(=O)NC(=O)/C=C/c1ccccc1OCc1ccncc1] | 5.0 |
| CG164 | 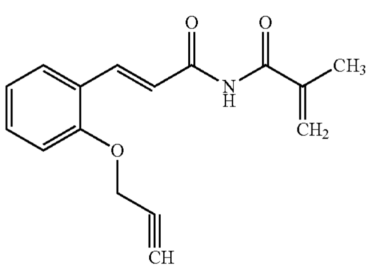 [SMILES: C#CCOc1ccccc1/C=C/C(=O)NC(=O)C(=C)C] | 3.5 |

TABLE 2-continued

| Name of Compounds | Compound Structure | Concentration at which STAT3 activity (p-STAT3) is inhibited by 50% (μM; $IC_{50}$) |
|---|---|---|
| CG165 | 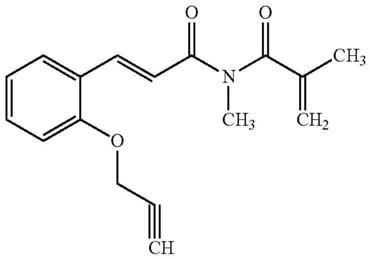 [SMILES: C#CCOc1ccccc1/C=C/C(=O)N(C)C(=O)C(=C)C] | 1.8 |
| CG168 | 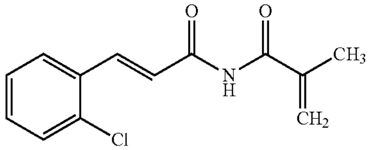 [SMILES: C=C(C)C(=O)NC(=O)/C=C/c1ccccc1Cl] | 2 |
| CG187 | 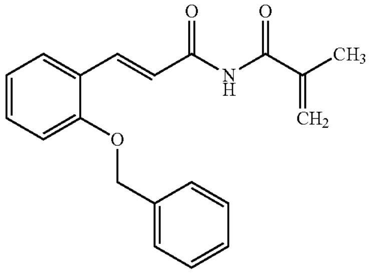 [SMILES: C=C(C)C(=O)NC(=O)/C=C/c1ccccc1OCc1ccccc1] | 3.5 |

As a result, it was confirmed that the cinnamamide derivative compounds of Chemical Formula 1 prepared in Synthesis Examples 1 to 8 of the present disclosure could inhibit STAT3 activity (p-STAT3) by more than 50%.

Next, the STAT3 phosphorylation inhibitory effect of the compound CG165 of the present disclosure in cancer cell lines was confirmed by Western blot.

As a result, as shown in FIGS. 2 and 3, it was confirmed that the treatment with the compound CG165 of the present disclosure inhibited STAT3 activity (p-STAT3) in a concentration-dependent manner in the prostate cancer cell line DU-145. In particular, it was confirmed that STAT3 activity (p-STAT3) was inhibited by more than 50% when treated at a concentration of 2 μM (FIG. 2).

In addition, it was confirmed that the treatment with the compound CG165 of the present disclosure inhibited STAT3 activity (p-STAT3) in a time-dependent manner in the prostate cancer cell line DU-145 (FIG. 3).

Example 2: Confirmation of Cancer Cell Growth Inhibitory Effect Due to STAT3 Phosphorylation Inhibition in Cancer Cell Lines-1

In Example 1, it was confirmed that STAT3 activity (p-STAT3) was inhibited in cancer cells when treated with the cinnamamide derivatives of Chemical Formula 1 prepared in Synthesis Examples 1 to 8. In order to confirm the effect of inhibiting STAT3 activity on inhibition of cancer cell growth, cell proliferation assay was performed using the prostate cancer cell line, a representative carcinoma.

Specifically, the prostate cancer cell line DU-145 ($0.8\times10^4$ cells) was plated in a 96-well plate. After 24 hours, DMSO (control) and CG-165 were treated for 24 or 48 hours according to concentration, and then treated with 10 ul of WST-1 reagent (Dojindo Laboratories, Kumamoto, Japan). After treatment for about 1 hour, cell viability was calculated using the absorbance measured at 450 nm with a microplate reader (Multiskan GO system, Thermo Fisher Scientific, Rockford, IL, USA).

As a result, as shown in FIG. 4, it was confirmed that the compound CG165 of the present disclosure inhibited the growth of cancer cells in a concentration-dependent manner.

Accordingly, it was confirmed that the compound CG165 of the present disclosure inhibited the growth of cancer cells by inhibiting the activity of STAT3 in cancer cells.

Example 3: Confirmation of Effect of the Compounds of the Present Disclosure on Normal Cells In order to confirm that the compound CG165 of the present disclosure does not affect the growth of normal cells, human foreskin fibroblasts HFF and MCF10A, human breast epithelial cells, were treated with CG-165 according to concentrations for 48 hours, and then the degree of cell viability was measured using the WST-1 assay (Dojindo Laboratories, Kumamoto, Japan).

As a result, as shown in FIG. 5, it was confirmed that the compound CG165 of the present disclosure had no significant effect on the growth of normal cells even when treated for 48 hours at a concentration of 10 μM.

Accordingly, it was confirmed that the compound CG165 of the present disclosure has little effect on normal cells and selectively inhibits the growth of cancer cells.

Example 4: Confirmation of STAT3 Phosphorylation Inhibitory Effect in Cancer Cell Lines-2

As an example of representative carcinomas other than prostate cancer cell line, the STAT3 phosphorylation inhibitory effect of the cinnamamide derivatives of Chemical Formula 1 prepared in Synthesis Examples 1 to 8 was confirmed in breast cancer cell line and lung cancer cell line by Western blot.

Specifically, the STAT3 phosphorylation inhibitory effect of CG165 of the present disclosure in breast cancer cell line MDA-MB-468 and lung cancer cell line HCC827 was confirmed by Western blot.

As a result, as shown in FIG. 6, it was confirmed that when the breast cancer cell line MDA-MB-468 and the lung cancer cell line HCC827 were treated with the compound CG165 of the present disclosure, STAT3 activity (p-STAT3) was inhibited in a concentration-dependent manner. In particular, it was confirmed that STAT3 activity (p-STAT3) was inhibited by more than 50% when treated at a concentration of 5 μM.

Example 5: Confirmation of Cancer Cell Growth Inhibitory Effect Due to STAT3 Phosphorylation Inhibition in Cancer Cell Lines-2

In Example 1, it was confirmed that STAT3 activity (p-STAT3) was inhibited by more than 50% in cancer cells when treated with the compound CG165 of the present disclosure. In order to confirm the effect of inhibiting STAT3 activity on inhibition of cancer cell growth, cell proliferation assay was performed using the breast cell line, a representative carcinoma.

Specifically, the breast cancer cell line MDA-MB-468 was treated with CG-165 according to concentrations for 24 or 48 hours, and then the degree of cell viability was measured using the WST-1 assay (Dojindo Laboratories, Kumamoto, Japan).

As a result, as shown in FIG. 7, it was confirmed that the compound CG165 of the present disclosure inhibited the growth of breast cancer cells in a concentration-dependent manner.

Accordingly, it was confirmed that the compound CG165 of the present disclosure inhibited the growth of cancer cells by inhibiting the activity of STAT3 in the prostate cancer cell line and breast cancer cell line, which are representative carcinomas.

Example 6: Confirmation of Inhibition of Expression and Apoptotic Effect of STAT3 Target Proteins in Cancer Cell Lines In Example 1, it was confirmed that STAT3 activity (p-STAT3) was inhibited in cancer cells when treated with the compound CG165 of the present disclosure. The effect of inhibiting the expression of STAT3 target proteins and the apoptotic effect due to the inhibition of STAT3 activity were confirmed using Western blot.

As a result, as shown in FIG. 8, it was confirmed that the compound CG165 of the present disclosure significantly inhibited the expression of cyclin A, Mcl-1, and survivin, which are target proteins of STAT3. In addition, it was confirmed that caspase 3, an enzyme related to cancer cell death, was activated, and as a result, the decomposition of PARP protein, a cell death biomarker, was promoted, thereby confirming that CG165 exhibited an anticancer effect through cell death.

Example 7: Confirmation of STAT3 Phosphorylation Inhibitory Effect in Natural Killer Cells (NKL)

The STAT3 phosphorylation inhibitory effect of CG165 prepared in Synthesis Example 3 or CG155 prepared in Synthesis Example 6 in natural killer cells (NKL), which are immune cells, was confirmed by Western blot.

Specifically, NKL ($4\times10^5$ cells) were plated in 6-well plate and each treated with 2 μM, 5 μM, and 10 μM of CG155 or CG165, and then the degree of STAT3 phosphorylation was measured by Western blot using p-STAT3 antibody.

As a result, as shown in FIG. 9, it was confirmed that the degree of phosphorylation of STAT3 in immune cells was inhibited in a concentration-dependent manner when treated with the compound CG155 or CG165 of the present disclosure. In addition, both compounds inhibited STAT3 activation by more than 90% when treated at 5 μM or more.

Accordingly, it was confirmed that the cinnamamide derivatives of the present disclosure have the ability to increase the activity of suicide cells.

Example 8: Confirmation of STAT3 Phosphorylation Inhibitory Effect in Bone Marrow-Derived Macrophages (BMDM)

Bone marrow-derived macrophages (BMDM) are cells isolated from the bone marrow and have various biological functions such as phagocytosis to remove pathogens and cell debris and inducing immune responses, etc. In order to study the function of macrophages, bone marrow-derived macrophages are used.

Accordingly, the STAT3 phosphorylation inhibitory effect of CG165 prepared in Synthesis Example 3 or CG155 prepared in Synthesis Example 6 in bone marrow-derived macrophages was confirmed by Western blot.

Specifically, 10 mL of RPMI1640 containing 10% fetal bovine serum (FBS), 1% penicillin/streptomycin, and 2 mM glutamine, a macrophage culture medium, was added to the bone lacuna between the bones of C57BL/6 mice, and bone marrow cells were collected therefrom. Bone marrow-derived macrophages were isolated and cultured from collected bone marrow cells using a reported method (J. Weischenfeldt, et al., *Cold Spring Harb. Protoc.* 3, 5080, 2008).

Subsequently, in order to confirm the function of CG155 and CG165 in inhibiting STAT3 activation in the bone marrow-derived macrophages isolated from mouse bone marrow, the bone marrow-derived macrophages were each pre-treated with DMSO, CG155 (5 μM, 10 μM), and CG165 (2 μM, 5 μM) for 1 hour. After removing the culture medium, the bone marrow-derived macrophages were treated with interleukin-10 (IL-10), a type of cytokine that can activate STAT3, for 15 minutes, and the function of CG155 and CG165 on inhibiting STAT3 activation was measured by Western blot using p-STAT3 antibody.

As a result, as shown in FIG. 10, it was confirmed that the degree of phosphorylation of STAT3 in macrophages was inhibited in a concentration-dependent manner when treated with the compound CG155 or CG165 of the present disclosure. In the case of CG165, when treated at 5 μM, it was confirmed that STAT3 activation was inhibited by more than 90%.

Accordingly, it was confirmed that the compounds of the present disclosure have the ability to regulate the activity of macrophages as well as suicide cells.

Example 9: Confirmation of Growth Inhibitory Effect of Cancer Tissue in Nude Mice It was attempted to evaluate the anticancer efficacy of the compound CG165 of the present disclosure by oral administration using nude mouse subcutaneous transplant models of human-derived prostate cancer (DU-145).

Specifically. Athymic-NCr NCr-nu specific pathogen-free (SPF) 5-week-old nude mice supplied by KOATECH (Pyeongtaek-si, Gyeonggi-do) were used as animals. The cancer cell concentration was adjusted to $3\times10^7$ cells/mL, and 0.3 mL of cell culture per mouse was injected subcutaneously into the axillary area between the right shoulder and chest wall. Subsequently, CG165 was prepared at the corresponding concentrations by adding DMAC 10%+Tween80 10%+ 20% HPβCD 80% step by step, and was administered orally at 0.2 mL per 20 g of mouse, which was repeated a total of 23 times for 30 days. At 30 days after starting drug administration, the DU-145 tumor was excised and its weight was measured.

As a result, as shown in FIG. 11, as of the final day (day 30), it was confirmed that there was a statistically significant decrease in tumor weight by 43.3% ($p<0.05$) and 64.3% ($p<0.05$) in CG165 (30 mg/kg)- or CG165 (60 mg/kg)-administered groups, respectively, compared to the vehicle.

In addition, as shown in FIG. 12, the results on the final day (day 30) showed that there was statistically significant tumor growth inhibition by 45.6% ($p<0.05$) and 63.3% ($p<0.05$) in CG165 (P.O, 30 mg/kg)- or CG165 (60 mg/kg)-administered groups, respectively, compared to the vehicle.

Meanwhile, as shown in FIG. 13, it was confirmed that no decrease in body weight was observed in the CG165 (30 mg/kg)- or CG165 (60 mg/kg)-administered group compared to the vehicle.

Accordingly, it was confirmed that the compound CG165 of the present disclosure effectively inhibited the growth of cancer tissue in animal models.

Next, it was attempted to evaluate the anticancer efficacy of the compound CG126 of the present disclosure by intraperitoneal administration using nude mouse subcutaneous transplant models of human-derived prostate cancer (DU-145) in the same manner as above.

As a result, as shown in FIG. 14, as of the final day (day 25), there was a statistically significant decrease in tumor weight by 54.2% ($p<0.06$) in the CG126 (30 mg/kg)-administered group compared to the vehicle.

Accordingly, it was confirmed that the compound CG126 of the present disclosure effectively inhibited the growth of cancer tissue in animal models.

Example 10: Verification of Single Oral Dose Toxicity in Mice

In order to obtain information on the acute toxicity of the compound CG165 of the present disclosure whose anticancer effect has been verified in animal models, the test substance was administered orally once at 100 mg/kg, 200 mg/kg, and 300 mg/kg to male mice to determine mortality, general symptoms, weight change, and post-mortem over 7 days.

Specifically, 20 Athymic-NCr NCr-nu specific pathogen-free (SPF) 5-week-old nude mice supplied by KOATECH (Pyeongtaek-si, Gyeonggi-do) were used as animals. Subsequently, CG165 was prepared as administration solution at different concentrations by adding DMAC 10%+Tween80 10%+20% HPβCD 80% step by step, and was administered orally.

General symptoms and dead animals were observed every hour from 1 to 6 hours after the final administration on the day of administration, and once daily from the day after administration until the 7th day for observation of changes in general symptoms, toxic symptoms, and the presence of dead animals.

In order to observe changes in body weight, the body weight of all animals used in the test was measured before administration and on days 0, 1, 2, 4, and 7 after administration.

On the 7th day after administration, all animals were anesthetized using $CO_2$ gas, laparotomized, and killed by exsanguination by cutting the abdominal artery and vein, and all internal organs were visually observed.

As a result, no dead animals were observed, and no general symptoms were observed due to administration of the test substance.

In addition, as shown in FIG. 15, it was confirmed that although changes in body weight was observed, there was no statistically significant weight loss until the final day of test after administration. No toxicological changes due to administration of the test substance were observed at the autopsy on the final day.

Accordingly, it was confirmed that the compound CG165 of the present disclosure did not cause toxicological changes upon single oral administration to male mice at doses of 100 mg/kg, 200 mg/kg, and 300 mg/kg.

In summary, it was confirmed that the novel cinnamamide derivative compounds of the present disclosure inhibited the activity of STAT3 in cancer cells, inhibited the expression of target molecules of STAT3, and induced cell death. Additionally, inhibition of STAT3 activity was confirmed in natural killer cells and macrophages, which are immune cells, and thus it was confirmed that the compounds of the present disclosure can increase anticancer effects by regulating the activity of immune cells. In addition, it was confirmed that the compounds of the present disclosure effectively inhibited the growth of cancer tissue in animal models.

Further, it was confirmed that the compounds of the present disclosure did not cause toxicological changes until a dose of 300 mg/kg in a single oral dose toxicity test.

Accordingly, the novel compounds of the present disclosure or pharmaceutically acceptable salts thereof exhibited the effects of inhibiting the growth of cancer cells and increasing the activity of immune cells in the tumor microenvironment by inhibiting STAT3 activity, and thus can be effectively used in the prevention or treatment of cancer.

Those of ordinary skill in the art will recognize that the present disclosure may be embodied in other specific forms without departing from its spirit or essential characteristics. The described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

The invention claimed is:

1. A compound represented by Chemical Formula 1 below, or a pharmaceutically acceptable salt thereof:

[Chemical Formula 1]

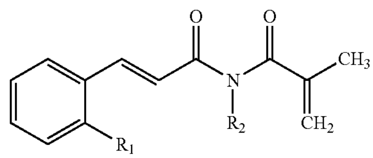

In Chemical Formula 1, $R_1$ is $C_{1-6}$ alkyl; hydroxy; halogen; $C_{1-6}$ alkynyloxy; or unsubstituted or substituted $C_{1-6}$ alkoxy;

wherein the substituted $C_{1-6}$ alkoxy contains $C_{1-6}$ aryl or 5- to 14-membered heteroaryl as a substituent, wherein the heteroaryl contains one or more O, N, or S, and $R_2$ is hydrogen or alkyl.

2. A pharmaceutical composition for treating cancer associated with signal transducers and activators of transcription 3 (STAT 3) activity, comprising a compound represented by Chemical Formula 1 below, or a pharmaceutically acceptable salt thereof, as an active ingredient:

[Chemical Formula 1]

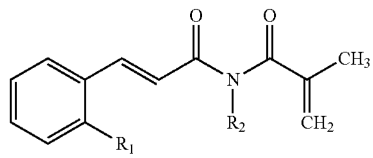

In Chemical Formula 1, $R_1$ is $C_{1-6}$ alkyl; hydroxy; halogen; $C_{1-6}$ alkynyloxy; or unsubstituted or substituted $C_{1-6}$ alkoxy;

wherein the substituted $C_{1-6}$ alkoxy contains $C_{1-6}$ aryl or 5- to 14-membered heteroaryl as a substituent, wherein the heteroaryl contains one or more O, N, or S, and $R_2$ is hydrogen or alkyl.

3. The composition of claim 2, wherein the composition inhibits the activity of signal transducers and activators of transcription 3 (STAT3).

4. The composition of claim 2, wherein the composition regulates the activity of natural killer cells or bone marrow-derived macrophages, which are immune cells, by inhibiting the activity of STAT3.

5. The composition of claim 2, wherein the cancer is any one selected from the group consisting of colorectal cancer, pancreatic cancer, gastric cancer, liver cancer, breast cancer, cervical cancer, thyroid cancer, parathyroid cancer, lung cancer, non-small cell lung cancer, prostate cancer, gallbladder cancer, bile duct cancer, non-Hodgkin's lymphoma, Hodgkin's lymphoma, blood cancer, bladder cancer, renal cancer, ovarian cancer, melanoma, colon cancer, bone cancer, skin cancer, head cancer, uterine cancer, rectal cancer, brain tumor, anal cancer, fallopian tube carcinoma, endometrial carcinoma, vaginal cancer, vulva carcinoma, esophageal cancer, small intestine cancer, endocrine cancer, adrenal cancer, soft tissue sarcoma, urethral cancer, penis cancer, ureter cancer, renal cell carcinoma, renal pelvic carcinoma, central nervous system tumor, primary central nervous system lymphoma, spinal cord tumor, brainstem glioma, and pituitary adenoma.

6. The composition of claim 2, wherein the composition further comprises a pharmaceutically acceptable carrier, excipient, or diluent.

7. The composition of claim 2, wherein the composition further comprises an anticancer agent.

8. The composition of claim 7, wherein the anticancer agent is any one selected from the group consisting of DNA alkylating agents, anticancer antibiotics, plant alkaloids, targeted anticancer agents, and cancer immunotherapy.

9. The composition of claim 7, wherein the anticancer agent is any one selected from the group consisting of mechlorethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin C, bleomycin, vincristine, vinblastine, paclitaxel, docetaxel, etoposide, teniposide, topotecan, irinotecan, imatinib, nilotinib, trastuzumab, gefitinib, sorafenib, ipilimumab, nivolumab, pembrolizumab, atezolizumab, durvalumab, and avelumab.

10. A method for treating cancer associated with signal transducers and activators of transcription 3 (STAT3) activity, comprising administering a pharmaceutical composition containing a compound represented by Chemical Formula 1 below, or a pharmaceutically acceptable salt thereof, as an active ingredient, into a subject:

[Chemical Formula 1]

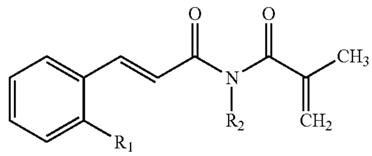

In Chemical Formula 1, $R_1$ is $C_{1-6}$ alkyl; hydroxy; halogen; $C_{1-6}$ alkynyloxy; or unsubstituted or substituted $C_{1-6}$ alkoxy;

wherein the substituted $C_{1-6}$ alkoxy contains $C_{1-6}$ aryl or 5- to 14-membered heteroaryl as a substituent, wherein the heteroaryl contains one or more O, N, or S, and $R_2$ is hydrogen or alkyl.

11. The method of claim 10, wherein the composition inhibits the activity of signal transducers and activators of transcription 3 (STAT3).

12. The composition of claim 2, wherein the cancer is any one selected from the group consisting of prostate cancer, breast cancer, lung cancer, pancreatic cancer, colorectal cancer, gastric cancer, and hepatocellular carcinoma.

* * * * *